United States Patent
Herron et al.

(10) Patent No.: US 9,793,497 B2
(45) Date of Patent: Oct. 17, 2017

(54) GREEN LUMINESCENT MATERIALS

(71) Applicant: E I DU PONT DE NEMOURS AND COMPANY, Wilmington, DE (US)

(72) Inventors: Norman Herron, Newark, DE (US); Weiying Gao, Landenberg, PA (US)

(73) Assignee: E I DU PONT DE NEMOURS AND COMPANY, Wilmington, DE (US)

(*) Notice: Subject to any disclaimer, the term of this patent is extended or adjusted under 35 U.S.C. 154(b) by 493 days.

(21) Appl. No.: 14/386,137

(22) PCT Filed: Mar. 21, 2013

(86) PCT No.: PCT/US2013/033209
§ 371 (c)(1),
(2) Date: Sep. 18, 2014

(87) PCT Pub. No.: WO2013/142634
PCT Pub. Date: Sep. 26, 2013

(65) Prior Publication Data
US 2015/0028321 A1  Jan. 29, 2015

Related U.S. Application Data

(60) Provisional application No. 61/614,848, filed on Mar. 23, 2012.

(51) Int. Cl.
| H01L 51/54 | (2006.01) |
| H01L 51/00 | (2006.01) |
| C09K 11/06 | (2006.01) |
| H05B 33/14 | (2006.01) |
| C07F 15/00 | (2006.01) |
| H01L 51/42 | (2006.01) |
| H01L 51/50 | (2006.01) |

(52) U.S. Cl.
CPC ...... *H01L 51/0085* (2013.01); *C07F 15/0033* (2013.01); *C09K 11/06* (2013.01); *H01L 51/42* (2013.01); *H01L 51/5028* (2013.01); *H05B 33/14* (2013.01); *C09K 2211/1007* (2013.01); *C09K 2211/1029* (2013.01); *C09K 2211/185* (2013.01); *H01L 51/5016* (2013.01); *H01L 2251/5384* (2013.01)

(58) Field of Classification Search
None
See application file for complete search history.

(56) References Cited

U.S. PATENT DOCUMENTS

| 6,699,599 | B2* | 3/2004 | Li et al. | H01L 51/0038 252/301.16 |
| 7,745,017 | B2* | 6/2010 | Nakamura et al. | C09K 11/06 257/40 |
| 7,816,016 | B1* | 10/2010 | Herron et al. | C07F 15/0033 257/40 |
| 2006/0127696 | A1* | 6/2006 | Stossel et al. | C07F 15/0033 257/40 |
| 2010/0140605 | A1* | 6/2010 | Shibata et al. | H01L 51/0087 257/40 |
| 2012/0175561 | A1* | 7/2012 | Franz et al. | C07F 15/0033 252/301.16 |

FOREIGN PATENT DOCUMENTS

WO   WO 2011/032626 A1 *   3/2011

OTHER PUBLICATIONS

Honda et al., "Synthesis and Spectral Properties of Tris(Terphenylylpyridine)Iridium and Tris(Tritylphenylpyridine)Iridium Complexes as Novel Electrophosphorescent Materials", Mol. Cryst. Liq. Cryst., vol. 455, pp. 373-379 (2006).*

* cited by examiner

Primary Examiner — Marie R. Yamnitzky

(57) ABSTRACT

There is provided a compound having Formula I

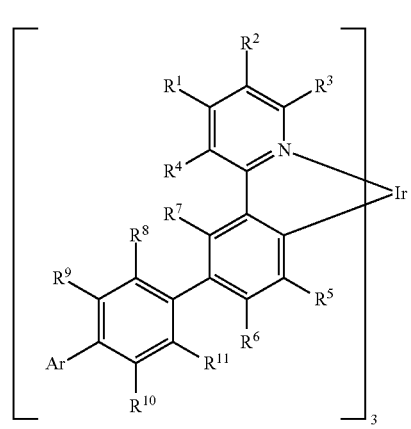

In the formula: Ar can be phenyl, biphenyl, or terphenyl, and can optionally have one or more substituents which can be D, alkyl, silyl, deuterated alkyl, or deuterated silyl; $R^1$ can be alkyl, silyl, aryl, heteroaryl, deuterated alkyl, deuterated silyl, deuterated aryl, or deuterated heteroaryl; $R^2$-$R^{11}$ are the same or different and can be H, D, alkyl, silyl, deuterated alkyl, or deuterated silyl.

14 Claims, 3 Drawing Sheets

GREEN LUMINESCENT MATERIALS

RELATED APPLICATION DATA

This application claims priority under 35 U.S.C. §119(e) from U.S. Provisional Application No. 61/614,848, filed on Mar. 23, 2012, which is incorporated by reference herein in its entirety.

BACKGROUND INFORMATION

Field of the Disclosure

This disclosure relates in general to green luminescent materials and their use in electronic devices.

Description of the Related Art

Organic electronic devices that emit light, such as light-emitting diodes that make up displays, are present in many different kinds of electronic equipment. In all such devices, an organic active layer is sandwiched between two electrical contact layers. At least one of the electrical contact layers is light-transmitting so that light can pass through the electrical contact layer. The organic active layer emits light through the light-transmitting electrical contact layer upon application of electricity across the electrical contact layers.

It is well known to use organic electroluminescent compounds as the active component in light-emitting diodes. Simple organic molecules, such as anthracene, thiadiazole derivatives, and coumarin derivatives are known to show electroluminescence. Metal complexes, particularly iridium and platinum complexes are also known to show electroluminescence. In some cases these small molecule materials are present as a dopant in a host material to improve processing and/or electronic properties.

There is a continuing need for new luminescent materials.

SUMMARY

There is provided a material having Formula I

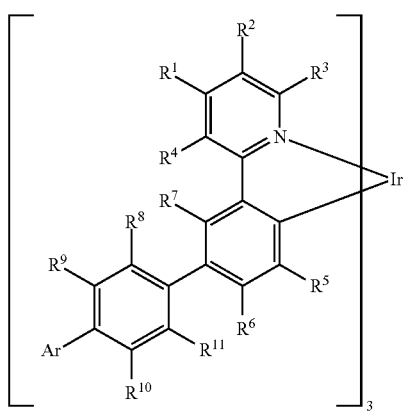

wherein:
Ar is selected from the group consisting of phenyl, biphenyl, and terphenyl, wherein Ar optionally has one or more substituents selected from the group consisting of D, alkyl, silyl, deuterated alkyl, and deuterated silyl;
$R^1$ is selected from the group consisting of H, D, alkyl, silyl, aryl, heteroaryl, deuterated alkyl, deuterated silyl, deuterated aryl, and deuterated heteroaryl; and
$R^2$-$R^{11}$ are the same or different and are selected from the group consisting of H, D, alkyl, silyl, deuterated alkyl, and deuterated silyl.

There is also provided an organic electronic device comprising a first electrical contact, a second electrical contact and a photoactive layer therebetween, the photoactive layer comprising the material having Formula I.

The foregoing general description and the following detailed description are exemplary and explanatory only and are not restrictive of the invention, as defined in the appended claims.

BRIEF DESCRIPTION OF THE DRAWINGS

Embodiments are illustrated in the accompanying figures to improve understanding of concepts as presented herein.

Figure 1:
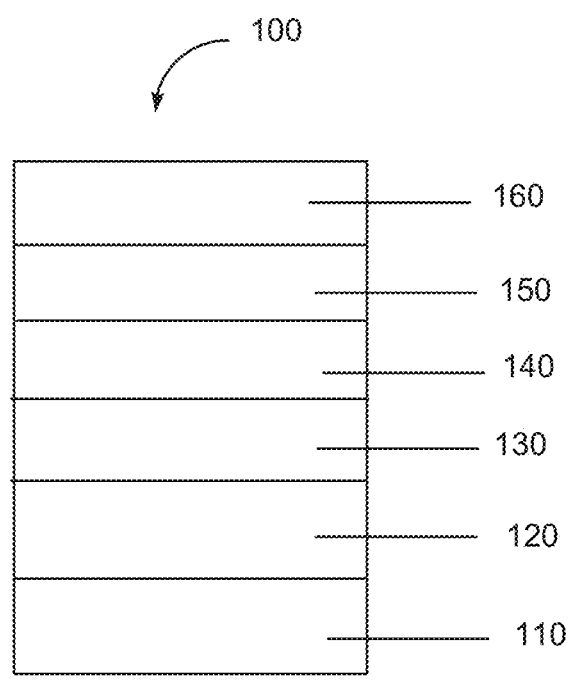
FIG. 1 includes an illustration of an organic light-emitting device.

Skilled artisans appreciate that objects in the figures are illustrated for simplicity and clarity and have not necessarily been drawn to scale. For example, the dimensions of some of the objects in the figures may be exaggerated relative to other objects to help to improve understanding of embodiments.

DETAILED DESCRIPTION

Many aspects and embodiments have been described above and are merely exemplary and not limiting. After reading this specification, skilled artisans appreciate that other aspects and embodiments are possible without departing from the scope of the invention.

Other features and benefits of any one or more of the embodiments will be apparent from the following detailed description, and from the claims. The detailed description first addresses Definitions and Clarification of Terms followed by the Material Having Formula I, Synthesis, Devices, and finally Examples.

1. Definitions and Clarification of Terms

Before addressing details of embodiments described below, some terms are defined or clarified.

The term "alkoxy" is intended to mean a group having the formula —OR, which is attached via the oxygen, where R is an alkyl.

The term "alkyl" is intended to mean a group derived from an aliphatic hydrocarbon and includes a linear, a branched, or a cyclic group. In some embodiments, an alkyl has from 1-20 carbon atoms.

The term "aromatic compound" is intended to mean an organic compound comprising at least one unsaturated cyclic group having delocalized pi electrons.

The term "aryl" is intended to mean a group derived from an aromatic hydrocarbon having one point of attachment. The term includes groups which have a single ring and those which have multiple rings which can be joined by a single bond or fused together. The term is intended to include heteroaryls. The term "arylene" is intended to mean a group derived from an aromatic hydrocarbon having two points of attachment. In some embodiments, an aryl group has from 3-60 carbon atoms.

The term "aryloxy" is intended to mean a group having the formula —OAr, which is attached via the oxygen, where Ar is an aryl.

The term "biphenyl" is intended to mean a group having two phenyl rings, as shown below.

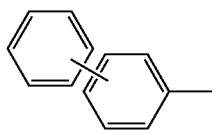

The term "branched alkyl" refers to an alkyl group having at least one secondary carbon (carbon bonded directly to two other carbons) or tertiary carbon (carbon bonded directly to three other carbons). The branched alkyl may be attached via any carbon in the chain.

The term "carbazolyl" refers to a group containing the unit

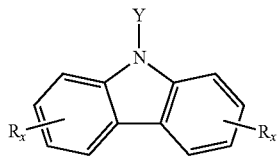

where R is the same or different at each occurrence and is selected from the group consisting of D, alkyl, aryl, or a point of attachment, x is the same or different and is 0-4, and Y is a point of attachment, alkyl, aryl, alkyl with a point of attachment, or aryl with a point of attachment. The term N-carbazolyl refers to a carbazolyl group where Y is the point of attachment.

The term "charge transport," when referring to a layer, material, member, or structure is intended to mean such layer, material, member, or structure facilitates migration of such charge through the thickness of such layer, material, member, or structure with relative efficiency and small loss of charge. Hole transport materials facilitate positive charge; electron transport materials facilitate negative charge. Although light-emitting materials may also have some charge transport properties, the term "charge transport layer, material, member, or structure" is not intended to include a layer, material, member, or structure whose primary function is light emission.

The term "deuterated" or "deuterated analog" is intended to mean that at least one H has been replaced by D. The term "deuterated analog" refers to a structural analog of a compound or group in which one or more available hydrogens have been replaced with deuterium. In a deuterated compound or deuterated analog, the deuterium is present in at least 100 times the natural abundance level.

The term "dopant" is intended to mean a material, within a layer including a host material, that changes the electronic characteristic(s) or the targeted wavelength(s) of radiation emission, reception, or filtering of the layer compared to the electronic characteristic(s) or the wavelength(s) of radiation emission, reception, or filtering of the layer in the absence of such material.

The term "electron-trap" or "electron-trap material" is intended to mean a compound that possesses a lowest unoccupied molecular orbital (LUMO) lying further in energy from the vacuum level than the LUMO of any other material present in the layer in which it is embedded. As such, it is the preferred site for negative charge to reside in that layer and if the trap material is present below the percolation volume (<~15%) such negative charge becomes localized upon molecules of the trap material presenting a hindrance to negative charge mobility within that layer.

The prefix "hetero" indicates that one or more carbon atoms have been replaced with a different atom. In some embodiments, the different atom is N, O, or S.

The term "hole-trap" or "hole-trap material" is intended to mean a compound that possesses a highest occupied molecular orbital (HOMO) lying closer in energy to the vacuum level than the HOMO of any other material present in the layer in which it is embedded. As such, it is the preferred site for positive charge to reside in that layer and, if the trap material is present below the percolation volume (<~15%), such positive charge becomes localized upon molecules of the trap material presenting a hindrance to positive charge mobility within that layer.

The term "host material" is intended to mean a material, usually in the form of a layer, to which a dopant may be added. The host material may or may not have electronic characteristic(s) or the ability to emit, receive, or filter radiation.

The terms "luminescent material" and "emitter" are intended to mean a material that emits light when activated by an applied voltage (such as in a light-emitting diode or light-emitting electrochemical cell). The term "green luminescent material" is intended to mean a material capable of emitting radiation that has an emission maximum at a wavelength in a range of approximately 495-569 nm. The term "orange luminescent material" is intended to mean a material capable of emitting radiation that has an emission maximum at a wavelength in a range of approximately 590-619 nm. The term "red luminescent material" is intended to mean a material capable of emitting radiation that has an emission maximum at a wavelength in a range of approximately 620-750 nm. The term "yellow luminescent material" is intended to mean a material capable of emitting radiation that has an emission maximum at a wavelength in a range of approximately 570-589 nm.

The term "layer" is used interchangeably with the term "film" and refers to a coating covering a desired area. The term is not limited by size. The area can be as large as an entire device or as small as a specific functional area such as the actual visual display, or as small as a single sub-pixel. Layers and films can be formed by any conventional deposition technique, including vapor deposition, liquid deposition (continuous and discontinuous techniques), and thermal transfer. Continuous deposition techniques, include but are not limited to, spin coating, gravure coating, curtain coating, dip coating, slot-die coating, spray coating, and continuous nozzle coating or printing. Discontinuous deposition techniques include, but are not limited to, ink jet printing, gravure printing, and screen printing.

The term "organic electronic device" or sometimes just "electronic device" is intended to mean a device including one or more organic semiconductor layers or materials.

The term "phosphorescent" as it refers to a material, is intended to mean a material which emits light from an excited state having significant triplet character.

The term "photoactive" refers to a material or layer that emits light when activated by an applied voltage (such as in a light emitting diode or chemical cell) or responds to radiant energy and generates a signal with or without an applied bias voltage (such as in a photodetector or a photovoltaic cell).

The term "siloxane" refers to the group $R_3SiO—$, where R is H, D, C1-20 alkyl, fluoroalkyl, or aryl. In some embodiments, one or more carbons in an R alkyl group are replaced with Si.

The term "silyl" refers to the group $R_3Si—$, where R is H, D, C1-20 alkyl, fluoroalkyl, or aryl. In some embodiments, one or more carbons in an R alkyl group are replaced with Si.

The term "terphenyl" refers to a group having three phenyl rings, as shown below.

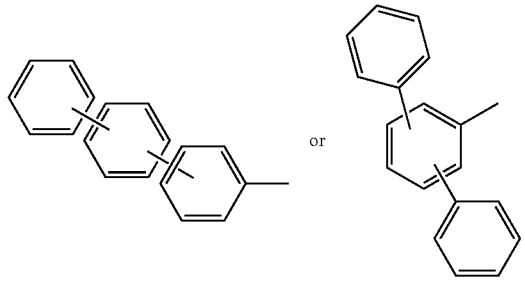

All groups may be unsubstituted or substituted. In some embodiments, the substituents are selected from the group consisting of deuterium ("D"), halide, alkyl, alkoxy, aryl, aryloxy, silyl, siloxane, alkylamino, arylamino, and cyano.

In this specification, unless explicitly stated otherwise or indicated to the contrary by the context of usage, where an embodiment of the subject matter hereof is stated or described as comprising, including, containing, having, being composed of or being constituted by or of certain features or elements, one or more features or elements in addition to those explicitly stated or described may be present in the embodiment. An alternative embodiment of the disclosed subject matter hereof, is described as consisting essentially of certain features or elements, in which embodiment features or elements that would materially alter the principle of operation or the distinguishing characteristics of the embodiment are not present therein. A further alternative embodiment of the described subject matter hereof is described as consisting of certain features or elements, in which embodiment, or in insubstantial variations thereof, only the features or elements specifically stated or described are present.

Also, use of "a" or "an" are employed to describe elements and components described herein. This is done merely for convenience and to give a general sense of the scope of the invention. This description should be read to include one or at least one and the singular also includes the plural unless it is obvious that it is meant otherwise.

Group numbers corresponding to columns within the Periodic Table of the elements use the "New Notation" convention as seen in the *CRC Handbook of Chemistry and Physics*, 81$^{st}$ Edition (2000-2001).

Unless otherwise defined, all technical and scientific terms used herein have the same meaning as commonly understood by one of ordinary skill in the art to which this invention belongs. Although methods and materials similar or equivalent to those described herein can be used in the practice or testing of embodiments of the present invention, suitable methods and materials are described below. All publications, patent applications, patents, and other references mentioned herein are incorporated by reference in their entirety, unless a particular passage is cited. In case of conflict, the present specification, including definitions, will control. In addition, the materials, methods, and examples are illustrative only and not intended to be limiting.

To the extent not described herein, many details regarding specific materials, processing acts, and circuits are conventional and may be found in textbooks and other sources within the organic light-emitting diode display, photodetector, photovoltaic, and semiconductive member arts.

2. Materials Having Formula I

The new materials described herein have Formula I

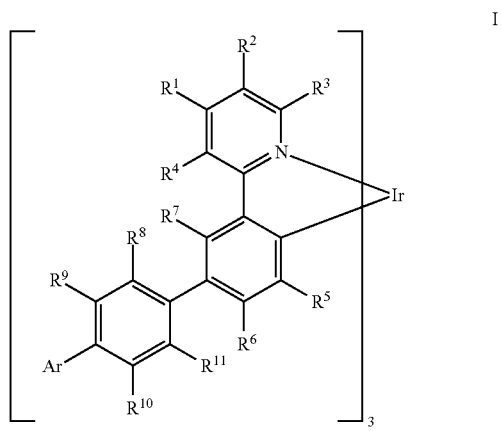

wherein:
Ar is selected from the group consisting of phenyl, biphenyl, and terphenyl, wherein Ar optionally has one or more substituents selected from the group consisting of D, alkyl, silyl, deuterated alkyl, and deuterated silyl;
$R^1$ is selected from the group consisting of H, D, alkyl, silyl, aryl, heteroaryl, deuterated alkyl, deuterated silyl, deuterated aryl, and deuterated heteroaryl; and
$R^2$-$R^{11}$ are the same or different and are selected from the group consisting of H, D, alkyl, silyl, deuterated alkyl, and deuterated silyl.

In some embodiments, the compounds having Formula I are useful as emissive materials. In some embodiments, the compounds are green emissive materials.

In some embodiments, the compounds having Formula I are used alone as emissive materials.

In some embodiments, the compounds having Formula I are used as an emissive dopant in a host material.

In some embodiments, the compounds having Formula I are green emissive materials and the green emission has color coordinates of x=0.20-0.35, and y=0.55-0.72, according to the C.I.E. chromaticity scale (Commision Internationale de L'Eclairage, 1931).

Compounds having a ligand with pyridine attached to a biphenyl group have been shown in the past. Unexpectedly, in some embodiments, compounds having Formula I have a narrower emission profile compared to prior art compounds. This is advantageous for display devices for producing more saturated green color.

Unexpectedly, in some embodiments, devices including compounds having Formula I have higher efficiency compared to devices including prior art compounds. This is advantageous for display devices and lighting devices for reducing energy consumption.

Unexpectedly, in some embodiments, devices including compounds having Formula I have longer lifetimes compared to devices including prior art compounds. This is advantageous for display and lighting applications.

In some embodiments of Formula I, Ar is selected from the group consisting of phenyl, 3-biphenyl, 4-biphenyl, 4,4'-terphenyl, 4,3'-terphenyl, 3,4'-terphenyl, 3,3'-terphenyl, 3,5-terphenyl, substituted phenyl, substituted 3-biphenyl, substituted 4-biphenyl, substituted 4,4'-terphenyl, substituted 4,3'-terphenyl, substituted 3,4'-terphenyl, substituted 3,3'-terphenyl, substituted 3,5-terphenyl, and deuterated analogs thereof.

In some embodiments of Formula I, $R^1$ is selected from the group consisting of alkyl having 1-20 carbons, silyl, deuterated alkyl having 1-20 carbons, and deuterated silyl.

In some embodiments of Formula I, $R^1$ is selected from the group consisting of phenyl, naphthyl, biphenyl, terphenyl, substituted derivatives thereof, and deuterated analogs thereof.

In some embodiments of Formula I, $R^1$ is selected from the group consisting of carbazolyl, phenyl-substituted carbazolyl, alkyl-substituted carbazolyl, and deuterated analogs thereof.

In some embodiments of Formula I, $R^1$ is selected from the group consisting of N-carbazolyl, phenyl-substituted N-carbazolyl, alkyl-substituted N-carbazolyl, and deuterated analogs thereof.

In some embodiments of Formula I, $R^2$-$R^{11}$ are selected from H and D.

In some embodiments of Formula I, at least one of $R^2$-$R^{11}$ is selected from alkyl, silyl, deuterated alkyl, and deuterated silyl.

Specific embodiments of the present invention include, but are not limited to, the following.

Embodiment 1

The compound of Formula I, wherein the compound is deuterated.

Embodiment 2

The compound of Formula I, wherein the compound is at least 10% deuterated. By "% deuterated" or "% deuteration" is meant the ratio of deuterons to the total of hydrogens plus deuterons, expressed as a percentage. The deuteriums may be on the same or different groups.

Embodiment 3

The compound of Formula I, wherein the compound is at least 20% deuterated.

Embodiment 4

The compound of Formula I, wherein the compound is at least 30% deuterated.

Embodiment 5

The compound of Formula I, wherein the compound is at least 40% deuterated.

Embodiment 6

The compound of Formula I, wherein the compound is at least 50% deuterated.

Embodiment 7

The compound of Formula I, wherein the compound is at least 60% deuterated.

Embodiment 8

The compound of Formula I, wherein the compound is at least 70% deuterated.

Embodiment 9

The compound of Formula I, wherein the compound is at least 80% deuterated.

Embodiment 10

The compound of Formula I, wherein the compound is at least 90% deuterated.

Embodiment 11

The compound of Formula I, wherein the compound is greater than 95% deuterated.

Embodiment 12

The compound of Formula I, wherein Ar is phenyl.

Embodiment 13

The compound of Formula I, wherein, Ar is 3-biphenyl.

Embodiment 14

The compound of Formula I, wherein Ar is 4-biphenyl.

Embodiment 15

The compound of Formula I, wherein Ar is 4,4'-terphenyl.

Embodiment 16

The compound of Formula I, wherein Ar is 4,3'-terphenyl.

Embodiment 17

The compound of Formula I, wherein Ar is 3,4'-terphenyl.

Embodiment 18

The compound of Formula I, wherein Ar is 3,3'-terphenyl.

Embodiment 19

The compound of Formula I, wherein Ar is 3,5-terphenyl.

Embodiment 20

The compound of Formula I, wherein Ar has at least one substituent.

Embodiment 21

The compound of any of Embodiments 12-19, wherein Ar has at least one substituent.

Embodiment 22

The compound of Embodiment 20 or 21, wherein the substituent is D.

Embodiment 23

The compound of Embodiment 20 or 21, wherein the substituent is an alkyl group having 1-20 carbons.

Embodiment 24

The compound of Embodiment 20 or 21, wherein the substituent is a silyl group.

Embodiment 25

The compound of Embodiment 23 or 24, wherein the substituent is deuterated.

Embodiment 26

The compound of Formula I, wherein $R^1$ is an alkyl group having 1-20 carbons.

Embodiment 27

The compound of Formula I, wherein $R^1$ is a deuterated alkyl group having 1-20 carbons.

Embodiment 28

The compound of Formula I, wherein $R^1$ is a branched alkyl group having 3-12 carbons.

Embodiment 29

The compound of Formula I, wherein $R^1$ is a deuterated branched alkyl group having 3-12 carbons.

Embodiment 30

The compound of Formula I, wherein $R^1$ is a silyl group having the formula $R_3Si—$, where R is the same or different at each occurrence and is an alkyl group having 1-12 carbons.

Embodiment 31

The compound of Formula I, wherein $R^1$ is a deuterated silyl group having the formula $R_3Si—$, where R is the same or different at each occurrence and is a deuterated alkyl group having 1-12 carbons.

Embodiment 32

The compound of Formula I, wherein $R^1$ is an aryl group.

Embodiment 33

The compound of Formula I, wherein $R^1$ is a deuterated aryl group.

Embodiment 34

The compound of Formula I, wherein $R^1$ is phenyl.

Embodiment 35

The compound of Formula I, wherein $R^1$ is naphthyl.

Embodiment 36

The compound of Formula I, wherein $R^1$ is biphenyl

Embodiment 37

The compound of Formula I, wherein $R^1$ is terphenyl.

Embodiment 38

The compound of Formula I, wherein $R^1$ is heteroaryl.

Embodiment 39

The compound of Formula I, wherein $R^1$ is deuterated heteroaryl.

Embodiment 40

The compound of Embodiment 38 or 39, wherein the heteroaryl or deuterated heteroaryl group is a nitrogen-containing group.

Embodiment 41

The compound of Formula I, wherein $R^1$ is carbazolyl.

Embodiment 42

The compound of Formula I, wherein $R^1$ is phenyl-substituted carbazolyl.

Embodiment 43

The compound of Formula I, wherein $R^1$ is alkyl group substituted carbazolyl.

Embodiment 44

The compound of any of Embodiments 41-43, wherein the carbazolyl is N-carbazolyl.

Embodiment 45

The compound of any of Embodiments 41-44, wherein $R^1$ is deuterated.

Embodiment 46

The compound of any of Embodiments 32-40, wherein $R^1$ has at least one substituent.

Embodiment 47

The compound of Embodiment 46, wherein the substituent is alkyl group having 1-20 carbons.

Embodiment 48

The compound of Embodiment 46, wherein the substituent is silyl group.

Embodiment 49

The compound of any of Embodiments 46-48, wherein the substituent is deuterated.

Embodiment 50

The compound of any of Embodiments 34-48, wherein $R^1$ has at least one substituent that is D.

Embodiment 51

The compound of Formula I, wherein $R^2$ is H.

Embodiment 52

The compound of Formula I, wherein $R^2$ is D.

Embodiment 53

The compound of Formula I, wherein $R^2$ is an alkyl group having 1-20 carbons.

Embodiment 54

The compound of Formula I, wherein $R^2$ is a silyl group having the formula $R_3Si-$, where R is the same or different at each occurrence and is an alkyl group having 1-12 carbons.

Embodiment 55

The compound of Formula I, wherein $R^3$ is H.

Embodiment 56

The compound of Formula I, wherein $R^3$ is D.

Embodiment 57

The compound of Formula I, wherein $R^3$ is an alkyl group having 1-20 carbons.

Embodiment 58

The compound of Formula I, wherein $R^3$ is a silyl group having the formula $R_3Si-$, where R is the same or different at each occurrence and is an alkyl group having 1-12 carbons.

Embodiment 59

The compound of Formula I, wherein $R^4$ is H.

Embodiment 60

The compound of Formula I, wherein $R^4$ is D.

Embodiment 61

The compound of Formula I, wherein $R^4$ is an alkyl group having 1-20 carbons.

Embodiment 62

The compound of Formula I, wherein $R^4$ is a silyl group having the formula $R_3Si-$, where R is the same or different at each occurrence and is an alkyl group having 1-12 carbons.

Embodiment 63

The compound of Formula I, wherein $R^5$ is H.

Embodiment 64

The compound of Formula I, wherein $R^5$ is D.

Embodiment 65

The compound of Formula I, wherein $R^5$ is an alkyl group having 1-20 carbons.

Embodiment 66

The compound of Formula I, wherein $R^5$ is a silyl group having the formula $R_3Si-$, where R is the same or different at each occurrence and is an alkyl group having 1-12 carbons.

Embodiment 67

The compound of Formula I, wherein $R^6$ is H.

Embodiment 68

The compound of Formula I, wherein $R^6$ is D.

Embodiment 69

The compound of Formula I, wherein $R^6$ is an alkyl group having 1-20 carbons.

Embodiment 70

The compound of Formula I, wherein $R^6$ is a silyl group having the formula $R_3Si-$, where R is the same or different at each occurrence and is an alkyl group having 1-12 carbons.

Embodiment 71

The compound of Formula I, wherein $R^7$ is H.

Embodiment 72

The compound of Formula I, wherein $R^7$ is D.

Embodiment 73

The compound of Formula I, wherein $R^7$ is an alkyl group having 1-20 carbons.

Embodiment 74

The compound of Formula I, wherein $R^7$ is a silyl group having the formula $R_3Si-$, where R is the same or different at each occurrence and is an alkyl group having 1-12 carbons.

Embodiment 75

The compound of Formula I, wherein $R^8$ is H.

Embodiment 76

The compound of Formula I, wherein $R^8$ is D.

Embodiment 77

The compound of Formula I, wherein $R^8$ is an alkyl group having 1-20 carbons.

Embodiment 78

The compound of Formula I, wherein $R^8$ is a silyl group having the formula $R_3Si$—, where R is the same or different at each occurrence and is an alkyl group having 1-12 carbons.

Embodiment 79

The compound of Formula I, wherein $R^9$ is H.

Embodiment 80

The compound of Formula I, wherein $R^9$ is D.

Embodiment 81

The compound of Formula I, wherein $R^9$ is an alkyl group having 1-20 carbons.

Embodiment 82

The compound of Formula I, wherein $R^9$ is a silyl group having the formula $R_3Si$—, where R is the same or different at each occurrence and is an alkyl group having 1-12 carbons.

Embodiment 83

The compound of Formula I, wherein $R^{10}$ is H.

Embodiment 84

The compound of Formula I, wherein $R^{10}$ is D.

Embodiment 85

The compound of Formula I, wherein $R^{10}$ is an alkyl group having 1-20 carbons.

Embodiment 86

The compound of Formula I, wherein $R^{10}$ is a silyl group having the formula $R_3Si$—, where R is the same or different at each occurrence and is an alkyl group having 1-12 carbons.

Embodiment 87

The compound of Formula I, wherein $R^{11}$ is H.

Embodiment 88

The compound of Formula I, wherein $R^{11}$ is D.

Embodiment 89

The compound of Formula I, wherein $R^{11}$ is an alkyl group having 1-20 carbons.

Embodiment 90

The compound of Formula I, wherein $R^{11}$ is a silyl group having the formula $R_3Si$—, where R is the same or different at each occurrence and is an alkyl group having 1-12 carbons.

Embodiment 91

The compound of any of Embodiments 53, 54, 57, 58, 61, 62, 65, 66, 69, 70, 73, 74, 77, 78, 81, 82, 85, 86, 89 or 90, wherein the group is deuterated.

Embodiment 92

The compound of Formula I, wherein $R^2$-$R^{11}$ are H.

Embodiment 93

The compound of Formula I, wherein $R^2$-$R^{11}$ are H or D.

Embodiment 94

The compound of Formula I, wherein at least one of $R^2$-$R^{11}$ is not H.

Embodiment 95

The compound of Formula I, wherein at least one of $R^2$-$R^{11}$ is an alkyl group.

Embodiment 96

The compound of Formula I, wherein at least one of $R^2$-$R^{11}$ is a silyl group.

Embodiment 97

The compound of Embodiment 94 or 95, wherein the group is deuterated.

Embodiment 98

The compound of Formula I, wherein Ar is selected from the group consisting of phenyl, 3-biphenyl, 4-biphenyl, 4,4'-terphenyl, 4,3'-terphenyl, 3,4'-terphenyl, 3,3'-terphenyl, 3,5-terphenyl, substituted phenyl, substituted 3-biphenyl, substituted 4-biphenyl, substituted 4,4'-terphenyl, substituted 4,3'-terphenyl, substituted 3,4'-terphenyl, substituted 3,3'-terphenyl, substituted 3,5-terphenyl, and deuterated analogs thereof, and $R^1$ is a branched alkyl.

Embodiment 99

The compound of Formula I, wherein Ar is selected from the group consisting of phenyl, 3-biphenyl, 4-biphenyl, 4,4'-terphenyl, 4,3'-terphenyl, 3,4'-terphenyl, 3,3'-terphenyl, 3,5-terphenyl, substituted phenyl, substituted 3-biphenyl, substituted 4-biphenyl, substituted 4,4'-terphenyl, substituted 4,3'-terphenyl, substituted 3,4'-terphenyl, substituted 3,3'-terphenyl, substituted 3,5-terphenyl, and deuterated analogs thereof, and $R^1$ is selected from the group consisting of phenyl, naphthyl, biphenyl, terphenyl, carbazolyl, substituted derivatives thereof, and deuterated analogs thereof.

Embodiment 100

The compound of Embodiment 98 or 99, wherein $R^2$-$R^{11}$ are selected from H and D.

Any of the above embodiments can be combined with one or more of the other embodiments, so long as they are not mutually exclusive. For example, the embodiment in which Ar is phenyl can be combined with the embodiment in which $R^1$ is a branched alkyl having 3-12 carbons. The same is true for the other non-mutually-exclusive embodiments discussed above. The skilled person would understand which embodiments were mutually exclusive and would thus readily be able to determine the combinations of embodiments that are contemplated by the present application.

Examples of materials having Formula I include, but are not limited to, compounds G1 through G17 shown below.

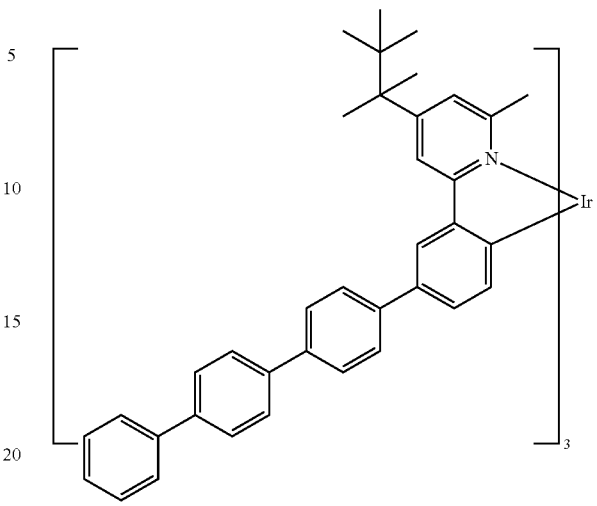
G3

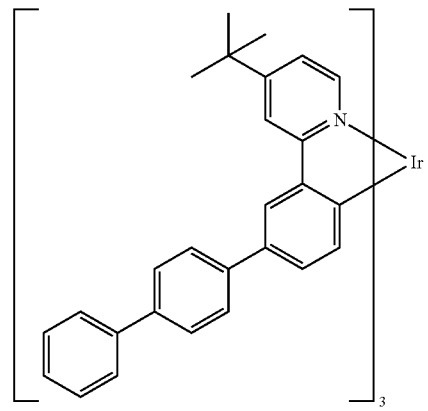
G1

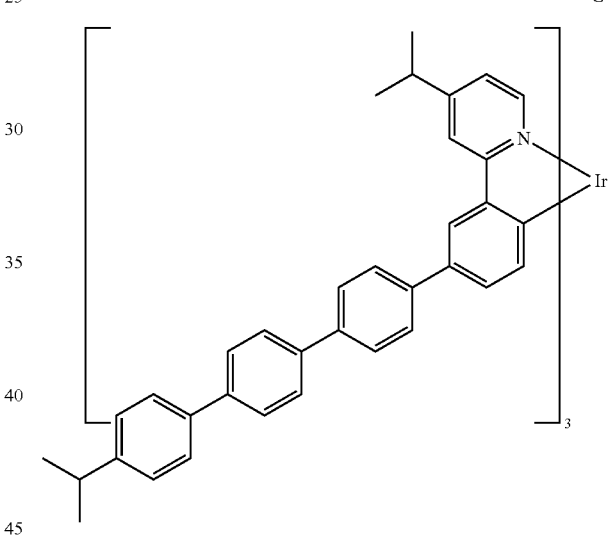
G4

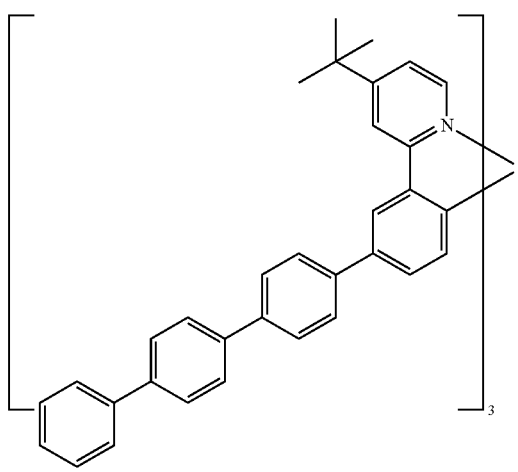
G2

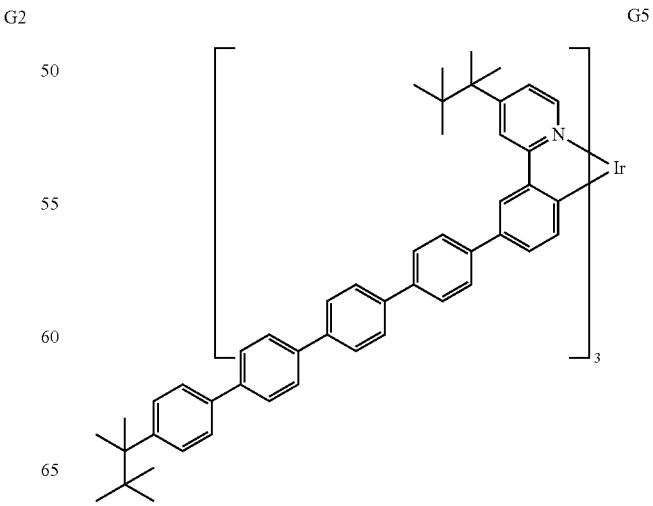
G5

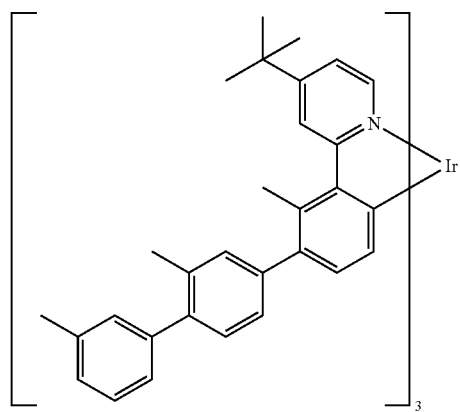
G6
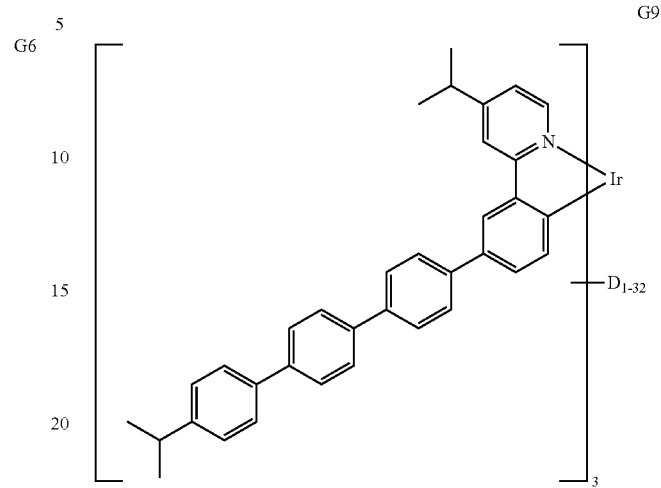
G9
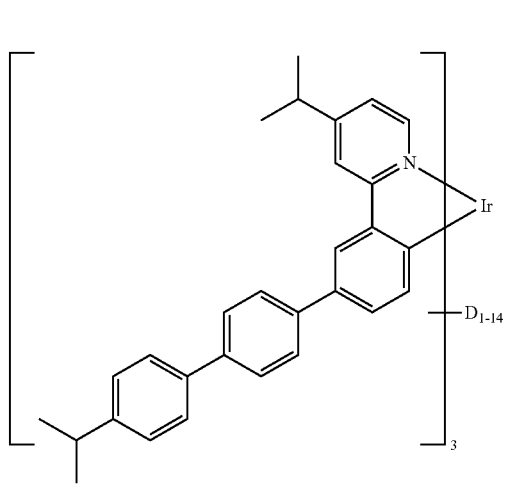
G7
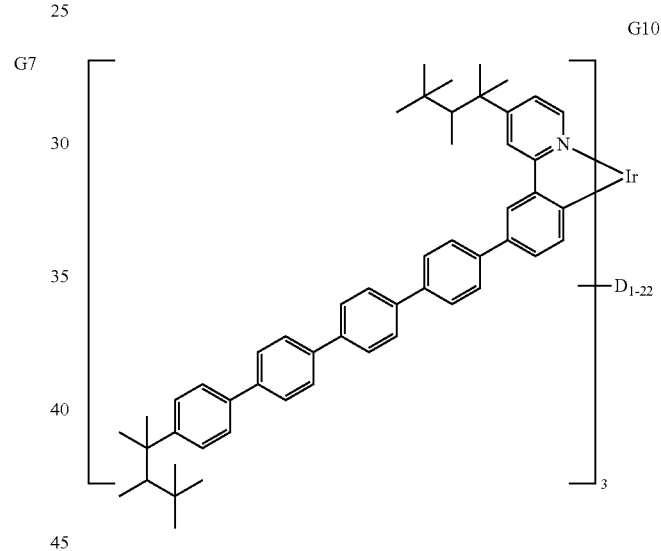
G10
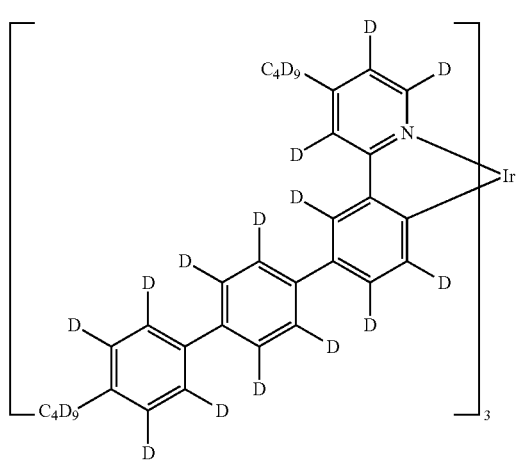
G8
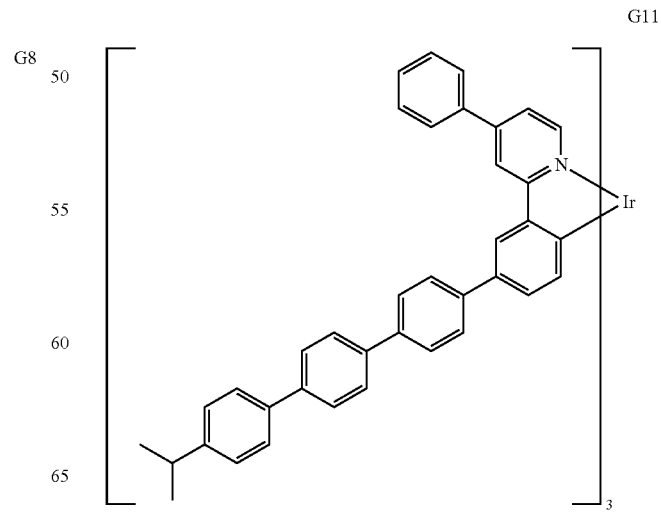
G11

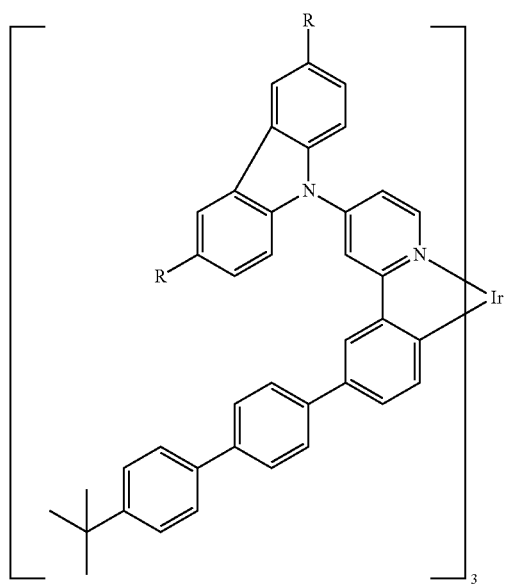

12a: R = phenyl
12b: R = 2-propyl

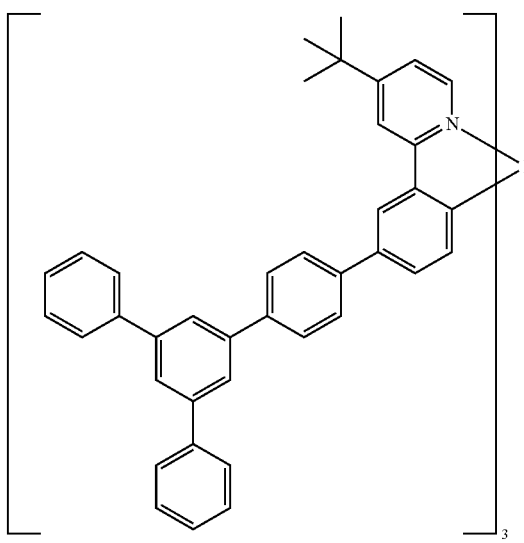

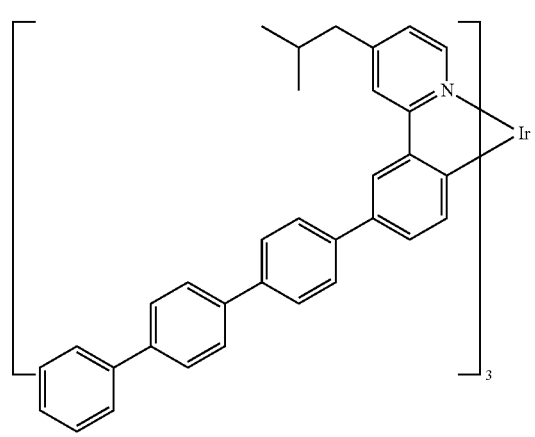

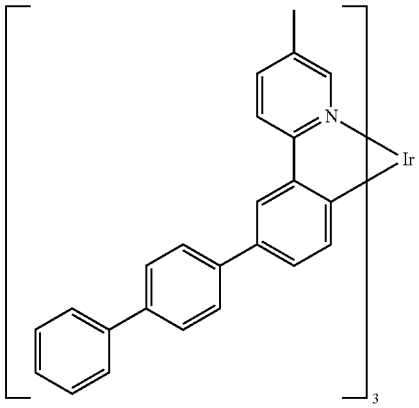

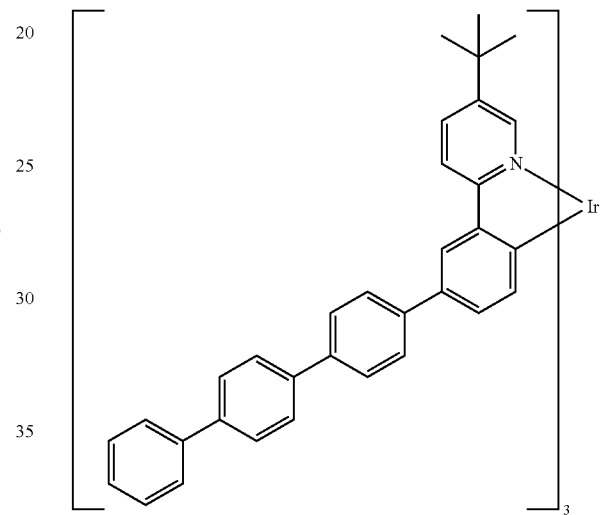

3. Synthesis

The materials described herein, are generally prepared by a procedure as follows. The ligand may most typically be prepared by Pd catalyzed Suzuki coupling between the appropriate 2-chloropyridine and the appropriate 3-chlorophenylboronic acid or ester followed by further Suzuki type coupling of the polyphenyl portion of the structure as depicted below:

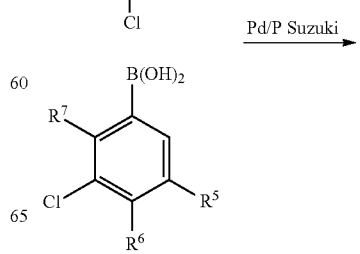

-continued

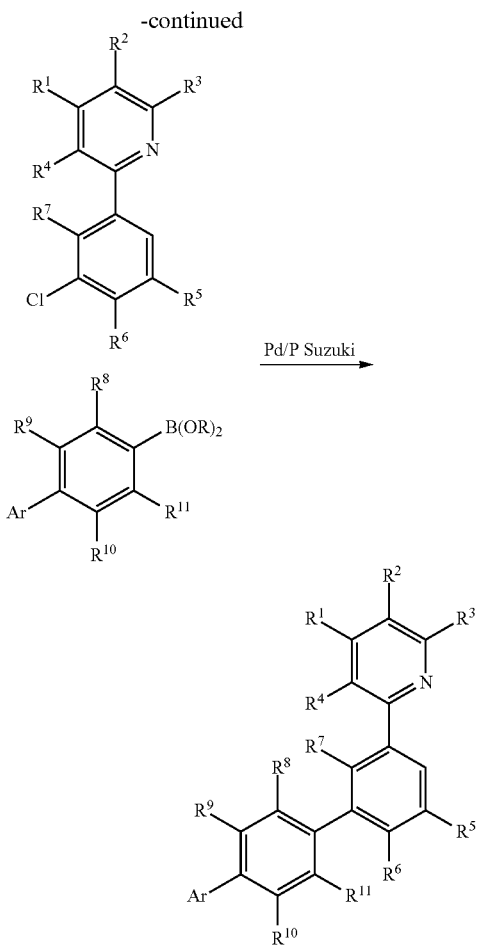

The ligand is then cyclometallated onto Ir using iridium trichloride in 2-ethoxyethanol at reflux to create the chlorodimeric intermediate. This step is followed by the third cyclometallization in alcohol solvent using silver salts to remove remaining chloride from the coordination sphere of the Ir. The isolated tris-cyclometallated material may be purified using chromatography, eluting with toluene or methylene chloride eluents and finally isolated by recrystallization from toluene or methylene chloride by addition of acetonitrile. The final yellow crystalline material is dried in high vacuum and then used, as isolated, in device construction. Individual details are presented below for specific compounds G1 and G2.

4. Devices

Organic electronic devices that may benefit from having one or more layers comprising the materials described herein include, but are not limited to, (1) devices that convert electrical energy into radiation (e.g., a light-emitting diode, light emitting diode display, lighting device, luminaire, or diode laser), (2) devices that detect signals through electronics processes (e.g., photodetectors, photoconductive cells, photoresistors, photoswitches, phototransistors, phototubes, IR detectors, biosensors), (3) devices that convert radiation into electrical energy, (e.g., a photovoltaic device or solar cell), and (4) devices that include one or more electronic components that include one or more organic semi-conductor layers (e.g., a transistor or diode).

One illustration of an organic electronic device structure is shown in FIG. 1. The device 100 has a first electrical contact layer, an anode layer 110 and a second electrical contact layer, a cathode layer 160, and a photoactive layer 140 between them. Adjacent to the anode is a hole injection layer 120. Adjacent to the hole injection layer is a hole transport layer 130, comprising hole transport material. Adjacent to the cathode may be an electron transport layer 150, comprising an electron transport material. As an option, devices may use one or more additional hole injection or hole transport layers (not shown) next to the anode 110 and/or one or more additional electron injection or electron transport layers (not shown) next to the cathode 160.

Layers 120 through 150 are individually and collectively referred to as the active layers.

Figure 2:
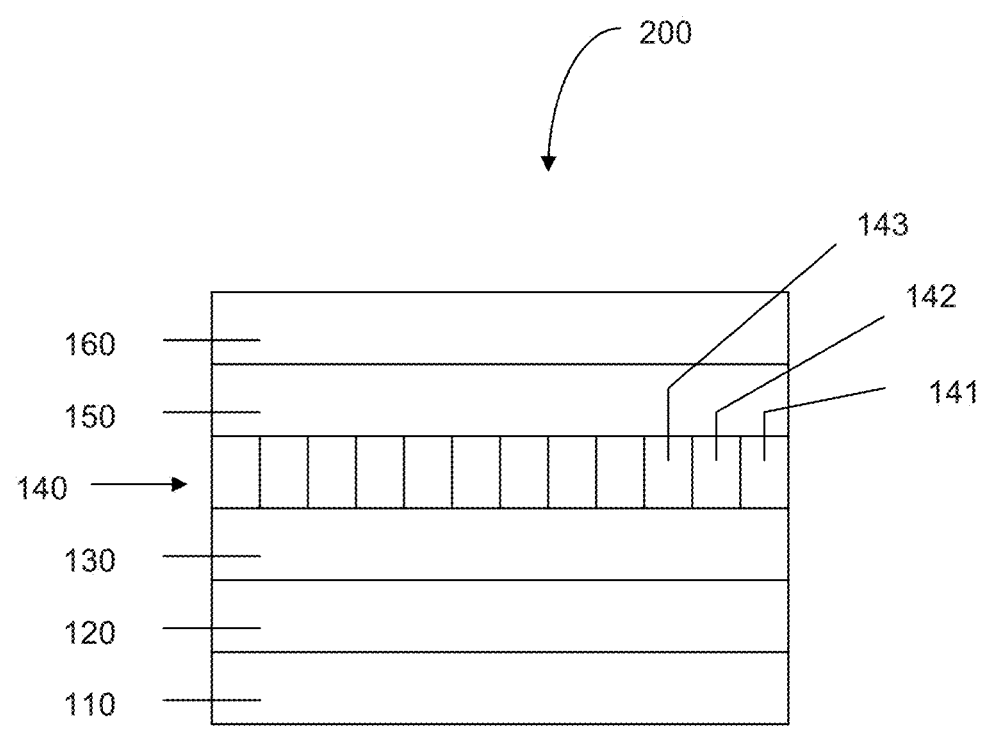
FIG. 2 includes another illustration of an organic light-emitting device.

In some embodiments, the photoactive layer is pixellated, as shown in FIG. 2. In device 200, layer 140 is divided into pixel or subpixel units 141, 142, and 143 which are repeated over the layer. Each of the pixel or subpixel units represents a different color. In some embodiments, the subpixel units are for red, green, and blue. Although three subpixel units are shown in the figure, two or more than three may be used.

In some embodiments, the different layers have the following range of thicknesses: anode 110, 500-5000 Å, in some embodiments, 1000-2000 Å; hole injection layer 120, 50-2000 Å, in some embodiments, 200-1000 Å; hole transport layer 120, 50-2000 Å, in some embodiments, 200-1000 Å; photoactive layer 130, 10-2000 Å, in some embodiments, 100-1000 Å; layer 140, 50-2000 Å, in some embodiments, 100-1000 Å; cathode 150, 200-10000 Å, in some embodiments, 300-5000 Å. The location of the electron-hole recombination zone in the device, and thus the emission spectrum of the device, can be affected by the relative thickness of each layer. The desired ratio of layer thicknesses will depend on the exact nature of the materials used.

In some embodiments, the compounds having Formula I are useful as the emissive material in photoactive layer 140, having green emission color. They can be used alone or as a dopant in a host material.

In some embodiments, the compounds having Formula I are useful as a hole-trap in photoactive layer 140.

In some embodiments, the compound having Formula I are useful as an electron-trap in photoactive layer 140.

Any of the compounds of Formula I represented by the embodiments, specific embodiments, and combination of embodiments discussed above can be used in the device.

a. Photoactive Layer

In some embodiments, the photoactive layer consists essentially of a compound having Formula I.

In some embodiments, the photoactive layer comprises a host material and a compound having Formula I as a dopant.

In some embodiments, the photoactive layer comprises a host material, a compound having Formula I as a dopant, and a second host material.

In some embodiments, the photoactive layer consists essentially of a host material and a compound having Formula I as a dopant.

In some embodiments, the photoactive layer consists essentially of a first host material, a second host material, and a compound having Formula I as a dopant.

In some embodiments, the weight ratio of dopant having Formula I to total host material is in the range of 1:99 to 40:60; in some embodiments 5:95 to 30:70; in some embodiments, 10:90 to 20:80.

In some embodiments, the host has a triplet energy level higher than that of the dopant, so that it does not quench the emission. In some embodiments, the host is selected from the group consisting of carbazoles, indolocarbazoles, triazines, aryl ketones, phenylpyridines, pyrimidines, phenanthrenes, triarylamines, triphenylenes, thiophenes, furans deuterated analogs thereof, combinations thereof, and mixtures thereof.

In some embodiments, the photoactive layer comprises a luminescent compound, a host material, and a compound having Formula I as a hole-trap material.

In some embodiments, the photoactive layer comprises a phosphorescent compound, a host material, and a compound having Formula I as a hole-trap material.

In some embodiments, the photoactive layer comprises a phosphorescent cyclometallated complex, a host material, and a compound having Formula I as a hole-trap material.

In some embodiments, the photoactive layer comprises a luminescent compound, a host material, and a compound having Formula I as a hole-trap material, and the luminescent compound has red, orange or yellow emission color.

In some embodiments, the photoactive layer comprises a luminescent compound, a host material, a compound having Formula I as a hole-trap material, and a second host material.

In some embodiments, the photoactive layer consists essentially of a luminescent compound, a host material, and a compound having Formula I as a hole-trap material.

In some embodiments, the photoactive layer consists essentially of a red luminescent compound, a host material, and a compound having Formula I as a hole-trap material.

In some embodiments, the photoactive layer consists essentially of a luminescent compound, a first host material, a second host material, and a compound having Formula I as a hole-trap material.

In some embodiments, the photoactive layer consists essentially of a red luminescent compound, a first host material, a second host material, and a compound having Formula I as a hole-trap material.

The hole-trap material of Formula I can be present in an amount of 1-10 wt % based on the total weight of the layer; in some embodiments, 2-5 wt %.

The compounds having Formula I can be used as a hole-trap for any kind of electroluminescent ("EL") layer for which any of the component HOMO levels are further from the vacuum level as compared to the HOMO level of the compound of Formula I. In addition, for fluorescent emissive materials, the emissive singlet energy level should be lower as compared to the singlet energy level of the compound of Formula I. This is discussed above in the definition section.

EL materials include, but are not limited to, small molecule organic fluorescent compounds, luminescent metal complexes, conjugated polymers, and mixtures thereof. Examples of fluorescent compounds include, but are not limited to, chrysenes, pyrenes, perylenes, rubrenes, coumarins, anthracenes, thiadiazoles, derivatives thereof, arylamino derivatives thereof, and mixtures thereof. Examples of metal complexes include, but are not limited to, metal chelated oxinoid compounds, such as tris(8-hydroxyquinolato)aluminum (Alq3); cyclometalated iridium and platinum electroluminescent compounds, such as complexes of iridium with phenylpyridine, phenylquinoline, or phenylpyrimidine ligands as disclosed in Petrov et al., U.S. Pat. No. 6,670,645 and Published PCT Applications WO 03/063555 and WO 2004/016710, and organometallic complexes described in, for example, Published PCT Applications WO 03/008424, WO 03/091688, and WO 03/040257, and mixtures thereof. Examples of conjugated polymers include, but are not limited to poly(phenylenevinylenes), polyfluorenes, poly(spirobifluorenes), polythiophenes, poly(p-phenylenes), copolymers thereof, and mixtures thereof.

Examples of red, orange and yellow light-emitting materials include, but are not limited to, complexes of Ir having phenylquinoline or phenylisoquinoline ligands, periflanthenes, fluoranthenes, and perylenes. Red light-emitting materials have been disclosed in, for example, U.S. Pat. No. 6,875,524, and published US application 2005-0158577.

In some embodiments, the photoactive layer comprises a luminescent compound, a host material, and a compound having Formula I as an electron-trap material.

In some embodiments, the photoactive layer comprises a phosphorescent compound, a host material, and a compound having Formula I as an electron-trap material.

In some embodiments, the photoactive layer comprises a phosphorescent cyclometallated complex, a host material, and a compound having Formula I as an electron-trap material.

In some embodiments, the photoactive layer comprises a luminescent compound, a host material, and a compound having Formula I as an electron-trap material, and the luminescent compound has red, orange or yellow emission color.

In some embodiments, the photoactive layer comprises a luminescent compound, a host material, a compound having Formula I as an electron-trap material, and a second host material.

In some embodiments, the photoactive layer consists essentially of a luminescent compound, a host material, and a compound having Formula I as an electron-trap material.

In some embodiments, the photoactive layer consists essentially of a red luminescent compound, a host material, and a compound having Formula I as an electron-trap material.

In some embodiments, the photoactive layer consists essentially of a luminescent compound, a first host material, a second host material, and a compound having Formula I as an electron-trap material.

In some embodiments, the photoactive layer consists essentially of a red luminescent compound, a first host material, a second host material, and a compound having Formula I as an electron-trap material.

The electron-trap material of Formula I can be present in an amount of 1-10 wt % based on the total weight of the layer; in some embodiments, 2-5 wt %.

The compounds having Formula I can be used as an electron-trap for any kind of electroluminescent ("EL") layer for which any of the component LUMO levels are closer to the vacuum level as compared to the LUMO level of the compound of Formula I. In addition, for fluorescent emissive materials, the emissive singlet energy level should be lower as compared to the singlet energy level of the compound of Formula I. This is discussed above in the definition section. The different types of EL materials are discussed above.

b. Other Device Layers

The other layers in the device can be made of any materials which are known to be useful in such layers.

The anode 110 is an electrode that is particularly efficient for injecting positive charge carriers. It can be made of, for example materials containing a metal, mixed metal, alloy, metal oxide or mixed-metal oxide, or it can be a conducting polymer, and mixtures thereof. Suitable metals include the Group 11 metals, the metals in Groups 4, 5, and 6, and the Group 8-10 transition metals. If the anode is to be light-transmitting, mixed-metal oxides of Groups 12, 13 and 14 metals, such as indium-tin-oxide, are generally used. The anode may also comprise an organic material such as polyaniline as described in "Flexible light-emitting diodes made from soluble conducting polymer," Nature vol. 357, pp 477 479 (11 June 1992). At least one of the anode and cathode should be at least partially transparent to allow the generated light to be observed.

The hole injection layer 120 comprises hole injection material and may have one or more functions in an organic electronic device, including but not limited to, planarization of the underlying layer, charge transport and/or charge injection properties, scavenging of impurities such as oxygen or metal ions, and other aspects to facilitate or to improve the performance of the organic electronic device. The hole injection layer can be formed with polymeric materials, such as polyaniline (PANI) or polyethylenedioxythiophene (PEDOT), which are often doped with protonic acids. The protonic acids can be, for example, poly(styrenesulfonic acid), poly(2-acrylamido-2-methyl-1-propanesulfonic acid), and the like.

The hole injection layer can comprise charge transfer compounds, and the like, such as copper phthalocyanine and the tetrathiafulvalene-tetracyanoquinodimethane system (TTF-TCNQ).

In some embodiments, the hole injection layer comprises at least one electrically conductive polymer and at least one fluorinated acid polymer.

In some embodiments, the hole injection layer is made from an aqueous dispersion of an electrically conducting polymer doped with a colloid-forming polymeric acid. Such materials have been described in, for example, published U.S. patent applications US 2004/0102577, US 2004/0127637, US 2005/0205860, and published PCT application WO 2009/018009.

Examples of hole transport materials for layer 130 have been summarized for example, in Kirk-Othmer Encyclopedia of Chemical Technology, Fourth Edition, Vol. 18, p. 837-860, 1996, by Y. Wang. Both hole transporting molecules and polymers can be used. Commonly used hole transporting molecules are: N,N'-diphenyl-N,N'-bis(3-methylphenyl)-[1,1'-biphenyl]-4,4'-diamine (TPD), 1,1-bis[(di-4-tolylamino) phenyl]cyclohexane (TAPC), N,N'-bis(4-methylphenyl)-N,N'-bis(4-ethylphenyl)[1,1'-(3,3'-dimethyl) biphenyl]-4,4'-diamine (ETPD), tetrakis-(3-methylphenyl)-N,N,N',N'-2,5-phenylenediamine (PDA), α-phenyl-4-N,N-diphenylaminostyrene (TPS), p-(diethylamino) benzaldehyde diphenylhydrazone (DEH), triphenylamine (TPA), bis[4-(N,N-diethylamino)-2-methylphenyl](4-methylphenyl)methane (MPMP), 1-phenyl-3-[p-(diethylamino) styryl]-5-[p-(diethylamino)phenyl]pyrazoline (PPR or DEASP), 1,2-trans-bis(9H-carbazol-9-yl)cyclobutane (DCZB), N,N,N',N'-tetrakis(4-methylphenyl)-(1,1'-biphenyl)-4,4'-diamine (TTB), N,N'-bis(naphthalen-1-yl)-N,N'-bis-(phenyl)benzidine (α-NPB), and porphyrinic compounds, such as copper phthalocyanine. In some embodiments, the hole transport layer comprises a hole transport polymer. In some embodiments, the hole transport polymer is a distyrylaryl compound. In some embodiments, the aryl group has two or more fused aromatic rings. In some embodiments, the aryl group is an acene. The term "acene" as used herein refers to a hydrocarbon parent component that contains two or more ortho-fused benzene rings in a straight linear arrangement. Other commonly used hole transporting polymers are polyvinylcarbazole, (phenylmethyl)-polysilane, and polyaniline. It is also possible to obtain hole transporting polymers by doping hole transporting molecules such as those mentioned above into polymers such as polystyrene and polycarbonate. In some cases, triarylamine polymers are used, especially triarylamine-fluorene copolymers. In some cases, the polymers and copolymers are crosslinkable.

In some embodiments, the hole transport layer further comprises a p-dopant. In some embodiments, the hole transport layer is doped with a p-dopant. Examples of p-dopants include, but are not limited to, tetrafluorotetracyanoquinodimethane (F4-TCNQ) and perylene-3,4,9,10-tetracarboxylic-3,4,9,10-dianhydride (PTCDA).

Examples of electron transport materials which can be used for layer 150 include, but are not limited to, metal chelated oxinoid compounds, including metal quinolate derivatives such as tris(8-hydroxyquinolato)aluminum (AlQ), bis(2-methyl-8-quinolinolato)(p-phenylphenolato) aluminum (BAlq), tetrakis-(8-hydroxyquinolato)hafnium (HfQ) and tetrakis-(8-hydroxyquinolato)zirconium (ZrQ); and azole compounds such as 2-(4-biphenylyl)-5-(4-t-butylphenyl)-1,3,4-oxadiazole (PBD), 3-(4-biphenylyl)-4-phenyl-5-(4-t-butylphenyl)-1,2,4-triazole (TAZ), and 1,3,5-tri (phenyl-2-benzimidazole)benzene (TPBI); quinoxaline derivatives such as 2,3-bis(4-fluorophenyl)quinoxaline; phenanthrolines such as 4,7-diphenyl-1,10-phenanthroline (DPA) and 2,9-dimethyl-4,7-diphenyl-1,10-phenanthroline (DDPA); and mixtures thereof. In some embodiments, the electron transport layer further comprises an n-dopant. N-dopant materials are well known. The n-dopants include, but are not limited to, Group 1 and 2 metals; Group 1 and 2 metal salts, such as LiF, CsF, and $Cs_2CO$; Group 1 and 2 metal organic compounds, such as Li quinolate; and molecular n-dopants, such as leuco dyes, metal complexes, such as $W_2(hpp)_4$ where hpp=1,3,4,6,7,8-hexahydro-2H-pyrimido-[1,2-a]-pyrimidine and cobaltocene, tetrathianaphthacene, bis(ethylenedithio)tetrathiafulvalene, heterocyclic radicals or diradicals, and the dimers, oligomers, polymers, dispiro compounds and polycycles of heterocyclic radical or diradicals.

The cathode 160, is an electrode that is particularly efficient for injecting electrons or negative charge carriers. The cathode can be any metal or nonmetal having a lower work function than the anode. Materials for the cathode can be selected from alkali metals of Group 1 (e.g., Li, Cs), the Group 2 (alkaline earth) metals, the Group 12 metals, including the rare earth elements and lanthanides, and the actinides. Materials such as aluminum, indium, calcium, barium, samarium and magnesium, as well as combinations, can be used.

Alkali metal-containing inorganic compounds, such as LiF, CsF, $Cs_2O$ and $Li_2O$, or Li-containing organometallic or coordination compounds can also be deposited between the organic layer 150 and the cathode layer 160 to lower the operating voltage. This layer, not shown, may be referred to as an electron injection layer.

It is known to have other layers in organic electronic devices. For example, there can be a layer (not shown) between the anode 110 and hole injection layer 120 to control the amount of positive charge injected and/or to provide band-gap matching of the layers, or to function as a protective layer. Layers that are known in the art can be used, such as copper phthalocyanine, silicon oxy-nitride, fluorocarbons, silanes, or an ultra-thin layer of a metal, such as Pt. Alternatively, some or all of anode layer 110, active layers 120, 130, 140, and 150, or cathode layer 160, can be surface-treated to increase charge carrier transport efficiency. The choice of materials for each of the component layers is preferably determined by balancing the positive and negative charges in the emitter layer to provide a device with high electroluminescence efficiency.

It is understood that each functional layer can be made up of more than one layer.

c. Device Fabrication

The device layers can be formed by any deposition technique, or combinations of techniques, including vapor deposition, liquid deposition, and thermal transfer.

In some embodiments, the device is fabricated by liquid deposition of the hole injection layer, the hole transport layer, and the photoactive layer, and by vapor deposition of the anode, the electron transport layer, an electron injection layer and the cathode.

The hole injection layer can be deposited from any liquid medium in which it is dissolved or dispersed and from which it will form a film. In some embodiments, the liquid medium consists essentially of one or more organic solvents. In some embodiments, the liquid medium consists essentially of water or water and an organic solvent. The hole injection material can be present in the liquid medium in an amount from 0.5 to 10 percent by weight. The hole injection layer can be applied by any continuous or discontinuous liquid deposition technique. In some embodiments, the hole injection layer is applied by spin coating. In some embodiments, the hole injection layer is applied by ink jet printing. In some embodiments, the hole injection layer is applied by continuous nozzle printing. In some embodiments, the hole injection layer is applied by slot-die coating. After liquid deposition, the liquid medium can be removed in air, in an inert atmosphere, or by vacuum, at room temperature or with heating.

The hole transport layer can be deposited from any liquid medium in which it is dissolved or dispersed and from which it will form a film. In some embodiments, the liquid medium consists essentially of one or more organic solvents. In some embodiments, the liquid medium consists essentially of water or water and an organic solvent. In some embodiments, the organic solvent is an aromatic solvent. In some embodiments, the organic liquid is selected from chloroform, dichloromethane, chlorobenzene, dichlorobenzene, toluene, xylene, mesitylene, anisole, and mixtures thereof. The hole transport material can be present in the liquid medium in a concentration of 0.2 to 2 percent by weight. The hole transport layer can be applied by any continuous or discontinuous liquid deposition technique. In some embodiments, the hole transport layer is applied by spin coating. In some embodiments, the hole transport layer is applied by ink jet printing. In some embodiments, the hole transport layer is applied by continuous nozzle printing. In some embodiments, the hole transport layer is applied by slot-die coating. After liquid deposition, the liquid medium can be removed in air, in an inert atmosphere, or by vacuum, at room temperature or with heating.

The photoactive layer can be deposited from any liquid medium in which it is dissolved or dispersed and from which it will form a film. In some embodiments, the liquid medium consists essentially of one or more organic solvents. In some embodiments, the liquid medium consists essentially of water or water and an organic solvent. In some embodiments, the organic solvent is an aromatic solvent. In some embodiments, the organic solvent is selected from chloroform, dichloromethane, toluene, anisole, 2-butanone, 3-pentanone, butyl acetate, acetone, xylene, mesitylene, chlorobenzene, tetrahydrofuran, diethyl ether, trifluorotoluene, and mixtures thereof. The photoactive material can be present in the liquid medium in a concentration of 0.2 to 2 percent by weight. Other weight percentages of photoactive material may be used depending upon the liquid medium. The photoactive layer can be applied by any continuous or discontinuous liquid deposition technique. In some embodiments, the photoactive layer is applied by spin coating. In some embodiments, the photoactive layer is applied by ink jet printing. In some embodiments, the photoactive layer is applied by continuous nozzle printing. In some embodiments, the photoactive layer is applied by slot-die coating. After liquid deposition, the liquid medium can be removed in air, in an inert atmosphere, or by vacuum, at room temperature or with heating.

The electron transport layer can be deposited by any vapor deposition method. In some embodiments, it is deposited by thermal evaporation under vacuum.

The electron injection layer can be deposited by any vapor deposition method. In some embodiments, it is deposited by thermal evaporation under vacuum.

The cathode can be deposited by any vapor deposition method. In some embodiments, it is deposited by thermal evaporation under vacuum.

EXAMPLES

The concepts described herein will be further described in the following examples, which do not limit the scope of the invention described in the claims.

Example 1

This example illustrates the preparation of Compound G1

(a) 2-(3-Chlorophenyl)-4-tert-butylpyridine

2-Chloro-4-tert-butylpyridine (19.92 grams, 0.1174 mol), 3-chlorophenylboronic acid (20.17 grams, 0.1290 mol), water (332 ml.), potassium carbonate (45.65 grams, 0.3303 mol), and monoglyme (332 ml.) were combined and sparged with nitrogen 45 minutes. Tetrakistriphenylphosphinepalladium(0) (4.98 grams, 5.746 mmol) was quickly added and the mixture was heated to reflux overnight. The mixture was concentrated by rotary evaporation to remove the monoglyme. Dichloromethane ("DCM") was added and extracted with water several times then preabsorbed to solid media. Silica chromatography with DCM and hexanes was used to purify the product which was concentrated to 27 grams of yellow oil.

(b) 2-[3-(4-biphenyl)phenyl]-4-tert-butylpyridine ligand

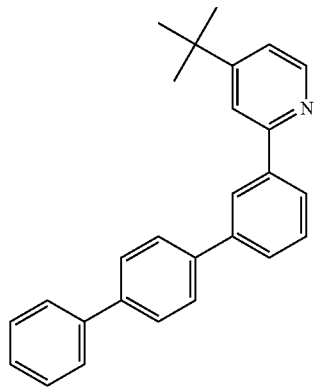 [SMILES: CC(C)(C)c1ccnc(-c2cccc(-c3ccc(-c4ccccc4)cc3)c2)c1]

2-(3-Chlorophenyl)-4-tert-butylpyridine (20 grams, 0.0814 mol), 4-biphenylboronic acid (20 grams, 0.1010 mol), a solution of water (250 ml.) and potassium phosphate tribasic (54 grams, 0.2544 mol), and 500 ml. of 1,4-dioxane were sparged with nitrogen 50 minutes. Tris(dibenzylideneacetone)dipalladium(0), (5.576 grams, 6.089 mmol) and tri-t-butylphosphine (3.415 grams, 16.879 mmol) was added quickly and the mixture refluxed overnight. The 1,4-Dioxane was removed by rotary evaporation and dichloromethane was added. After several water washes the organics were preabsorbed to solid media and purified by silica column chromatography with DCM and hexanes. Product was concentrated by rotary evaporation to 25.27 grams of yellow oil which partly solidified overnight.

(c) Compound G1

15 g ligand from part (b) was mixed with 7.5 g iridium chloride in 20 mL 2-ethoxyethanol, and 2 mL water. The mixture was refluxed under nitrogen overnight, cooled and diluted with 20 mL water. A bright yellow orange solid was filtered, washed well with water and methanol, and suctioned dry. The solid was extracted into dichloromethane, filtered and dried. This solid was added into 150 mL methylene chloride and 10 mL methanol and 5 g silver trifluoromethane sulfonate was added. This was stirred well and refluxed for 4 hrs. After cooling, the mixture was evaporated, extracted into methanol and filtered. All but 4 g of the solid was taken into n-propanol (~80 mL) with 7 g ligand from step (b) and refluxed overnight. The yellow solid was separated by filtration and washed with methanol. The n-propanol filtrate was further heated at reflux to drive further reaction and then evaporated to dryness. The recovered yellow solid was then combined with the first isolated fraction and dissolved in dry toluene. The material was purified by chromatography using toluene eluent. The final yellow eluent from this was evaporated to low volume and acetonitrile was added to ~50% by volume and the resultant solution allowed to stand as yellow crystals were generated. Filtration of the yellow product and drying in high vacuum. yielded approximately 9.7 g product G1 identified as the fac isomer by 1-H nmr spectroscopy and with purity >99% as judged by ultra high pressure liquid chromatography.

Example 2

This example illustrates the preparation of Compound G2

(b) 2-[3-(4-terphenyl)phenyl]-4-tert-butylpyridine ligand

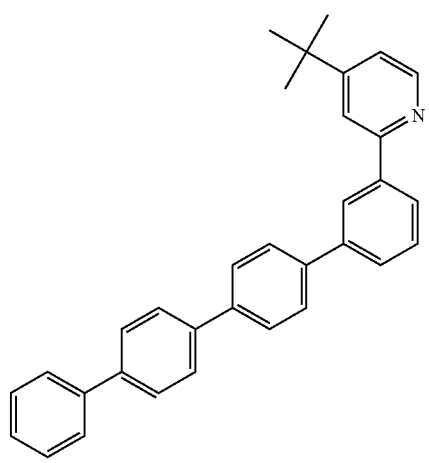 [SMILES: CC(C)(C)c1ccnc(-c2cccc(-c3ccc(-c4ccc(-c5ccccc5)cc4)cc3)c2)c1]

2-(3-Chlorophenyl)-4-tert-butylpyridine (10 grams, 0.0407 mol) from example 1 above, 4,4'-terphenylboronic acid (13.7 grams, 0.05 mol), a solution of water (125 ml.) and potassium phosphate tribasic (27 grams, 0.1272 mol), and 250 ml. of 1,4-dioxane were sparged with nitrogen 50 minutes. Tris(dibenzylideneacetone)dipalladium(0), (2.288 grams, 3.044 mmol) and tri-t-butylphosphine (1.708 grams, 8.44 mmol) was added quickly and the mixture refluxed overnight. The 1,4-dioxane was removed by rotary evaporation and dichloromethane was added. After several water washes the organics were preabsorbed to solid media and purified by silica column chromatography with DCM and hexanes. Product was concentrated by rotary evaporation to 8 grams of very pale yellow solid.

(c) Compound G2

2.65 g ligand from part (b) was mixed with 1.1 g iridium chloride in 20 mL 2-ethoxyethanol, and 2 mL water. The mixture was refluxed under nitrogen overnight, cooled and diluted with 20 mL water. A bright yellow solid was filtered, washed well with water and methanol, and suctioned dry. The solid was extracted into dichloromethane, filtered and dried. This solid was added into 150 mL DCM and 10 mL methanol and 2.5 g silver trifluoromethane sulfonate was added. This was stirred well and gently refluxed for 4 hrs. After cooling, the mixture was evaporated, extracted into 50/50-methylene chloride/methanol and filtered. The recovered orange solution was evaporated to dryness and redissolved into 50 mL 2-ethoxyethanol along with 2 g ligand from step (b) and refluxed overnight. Addition of 1 g sodium carbonate to the resultant cooled solution generated copious yellow solid which was further refluxed for 2 hrs and was then separated by filtration and washed with methanol and suction dried. The material was extracted into methylene chloride and purified by chromatography, using methylene chloride eluent. The final yellow eluent was evaporated to low volume and acetonitrile was added to ~50% by volume and the resultant solution allowed to stand as yellow needle crystals were generated. Filtration of the yellow product and drying in high vacuum. yielded approximately 2.4 g product G2 identified as the fac isomer by 1-H nmr spectroscopy and with purity >99% as judged by ultra high pressure liquid chromatography.

Example 3

Compound G16 was made in a manner analogous to Example 1, starting with 2-chloro-5-methylpyridine.

DEVICE EXAMPLES

These examples demonstrate the fabrication and performance of OLED devices.
(1) Materials
HIJ-1 is an electrically conductive polymer doped with a polymeric fluorinated sulfonic acid. Such materials have been described in, for example, published U.S. patent applications US 2004/0102577, US 2004/0127637, US 2005/0205860, and published PCT application WO 2009/018009.
HT-1 is a triarylamine-containing polymer. Such materials have been described in, for example, published PCT application WO 2009/067419.
Host-1 is an indolocarbazole. Such materials have been described in copending patent application [UC1006], published as US 2013-0248849.

Host-2 is an indolocarbazole. Such materials have been described in, for example, published PCT applications WO 2010/099534 and WO 2011/059463.

Host-3 is an indolocarbazole. Such materials have been described in, for example, published PCT applications WO 2010/099534 and WO 2011/059463.

ET-1 is a metal quinolate complex.

Dopant-1 has the formula below, and can be made as described in US patent publication 2006/0008673.

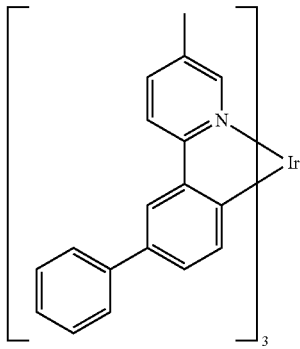

The devices had the following structure on a glass substrate:
anode=Indium Tin Oxide (ITO), 50 nm
hole injection layer=HIJ-1 (50 nm)
hole transport layer=HT-1 (20 nm)
photoactive layer, discussed below =35:49:16 (weight ratio)
Host-1:Host-2:dopant (60 nm);
electron transport layer=ET-1 (10 nm)
electron injection layer/cathode=CsF/Al (0.7/100 nm)
(2) Device Fabrication OLED devices were fabricated by a combination of solution processing and thermal evaporation techniques. Patterned indium tin oxide (ITO) coated glass substrates from Thin Film Devices, Inc were used. These ITO substrates are based on Corning 1737 glass coated with ITO having a sheet resistance of 30 ohms/square and 80% light transmission. The patterned ITO substrates were cleaned ultrasonically in aqueous detergent solution and rinsed with distilled water. The patterned ITO was subsequently cleaned ultrasonically in acetone, rinsed with isopropanol, and dried in a stream of nitrogen.

Immediately before device fabrication the cleaned, patterned ITO substrates were treated with UV ozone for 10 minutes. Immediately after cooling, an aqueous dispersion of HIJ-1 was spin-coated over the ITO surface and heated to remove solvent. After cooling, the substrates were then spin-coated with a solution of HT-1, and then heated to remove solvent. After cooling the substrates were spin-coated with a solution of the photoactive layer materials in methyl benzoate and heated to remove solvent. The substrates were masked and placed in a vacuum chamber. The electron transport layer was deposited by thermal evaporation, followed by a layer of CsF. Masks were then changed in vacuo and a layer of Al was deposited by thermal evaporation. The chamber was vented, and the devices were encapsulated using a glass lid, desiccant, and UV curable epoxy.

(3) Device Characterization

The OLED samples were characterized by measuring their (1) current-voltage (I-V) curves, (2) electroluminescence radiance versus voltage, and (3) electroluminescence spectra versus voltage. All three measurements were performed at the same time and controlled by a computer. The current efficiency of the device at a certain voltage is determined by dividing the electroluminescence radiance of the LED by the current density needed to run the device. The unit is a cd/A. The color coordinates were determined using either a Minolta CS-100 meter or a Photoresearch PR-705 meter.

Example 4 and Comparative Example A

This example illustrates the use of a compound having Formula I as the light emitting material in a device.

In Example 4, the photoactive layer contained Compound G1 as the light-emitting material.

In Comparative Example A, the photoactive layer contained Dopant-1 as the light-emitting material.

The results are given in Table 1 below.

TABLE 1

| | Device results | | | | | |
|---|---|---|---|---|---|---|
| Example | C.E. (cd/A) | E.Q.E. (%) | CIE (x, y) | T50 (hours) | ADT50 at Display luminance (hours) | Display luminance (nits) |
| Comp. A | 67.7 | 18.3 | 0.316, 0.636 | 150347 | 57421 | 1707 |
| Ex. 4 | 66.5 | 18.0 | 0.302, 0.644 | 181079 | 71402 | 1677 |

All data @ 1000 nits, unless specified otherwise; CE = current efficiency; E.Q.E. is the external quantum efficiency; CIEx and CIEy are the x and y color coordinates according to the C.I.E. chromaticity scale (Commission Internationale de L'Eclairage, 1931); T50 is to time to reach 50% of initial luminance at 1000 nits; ADT50 is the adjusted time to reach 50% luminance at display luminance.

It can be seen from Table 1 that the while the efficiency is nearly the same, the device with the Compound G1 has better color and the lifetime is increased by over 20%.

Figure 3:
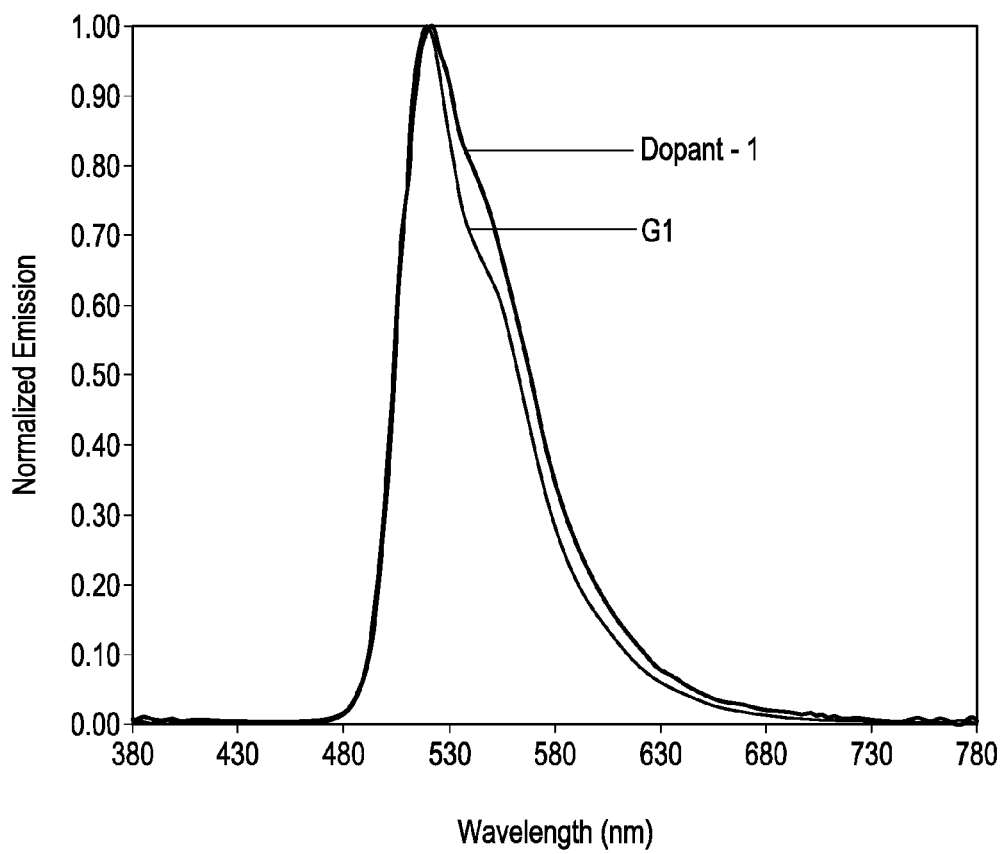
FIG. 3 includes emission spectra for two light-emitting complexes.

In FIG. 3, the emission spectra are shown for Compound G1 and Dopant-1. The spectrum is narrower for Compound G1 than for Dopant-1.

Example 5 and Comparative Example B

Devices were prepared as described above, except for the photoactive layer. The photoactive layer was 60 nm of 84:16 (weight ratio) Host-3:dopant.

In Example 5, the dopant was Compound G16.

In Comparative Example B, the dopant was Dopant-1.

The results are shown in Table 2 below.

TABLE 2

| | Device Results | | | | | |
|---|---|---|---|---|---|---|
| Example | C.E. (cd/A) | E.Q.E. (%) | CIE (x, y) | T50 (hours) | ADT50 at Display luminance (hours) | Display luminance (nits) |
| Comp. B | 71.8 | 19.5 | 0.321, 0.632 | 89,491 | 33,716 | 1720 |
| Ex. 5 | 72.9 | 19.5 | 0.322, 0.635 | 111,188 | 41,077 | 1718 |

All data @ 1000 nits, unless specified otherwise; CE = current efficiency; E.Q.E. is the external quantum efficiency; CIEx and CIEy are the x and y color coordinates according to the C.I.E. chromaticity scale (Commission Internationale de L'Eclairage, 1931); T50 is to time to reach 50% of initial luminance at 1000 nits; ADT50 is the adjusted time to reach 50% luminance at display luminance.

It can be seen that with Compound G16, the color is very similar to the comparative dopant, however the lifetime is increased by 20%.

Note that not all of the activities described above in the general description or the examples are required, that a portion of a specific activity may not be required, and that one or more further activities may be performed in addition to those described. Still further, the order in which activities are listed are not necessarily the order in which they are performed.

In the foregoing specification, the concepts have been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

It is to be appreciated that certain features are, for clarity, described herein in the context of separate embodiments, may also be provided in combination in a single embodiment. Conversely, various features that are, for brevity, described in the context of a single embodiment, may also be provided separately or in any subcombination. Further, reference to values stated in ranges include each and every value within that range.

What is claimed is:

1. An organic electronic device comprising a first electrical contact, a second electrical contact, and a photoactive layer therebetween, wherein the photoactive layer comprises a luminescent compound having red, orange, or yellow emission color, a host material, and a compound having Formula I

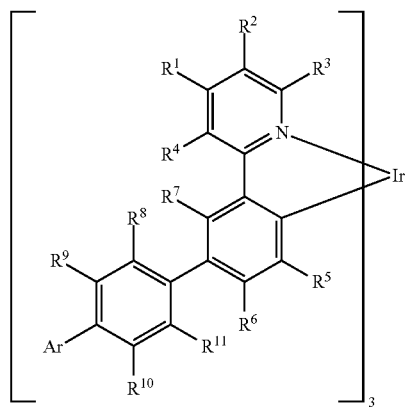

wherein:
Ar is selected from the group consisting of phenyl, biphenyl, and terphenyl, wherein Ar optionally has one or more substituents selected from the group consisting of D, alkyl, silyl, deuterated alkyl, and deuterated silyl;
$R^1$ is selected from the group consisting of H, D, alkyl, silyl, aryl, heteroaryl, deuterated alkyl, deuterated silyl, deuterated aryl, and deuterated heteroaryl; and
$R^2$-$R^{11}$ are the same or different and are selected from the group consisting of H, D, alkyl, silyl, deuterated alkyl, and deuterated silyl;
wherein the compound having Formula I is present as a hole-trap material which possesses a highest occupied molecular orbital (HOMO) lying closer in energy to the vacuum level than the HOMO of any other material present in the photoactive layer.

2. An organic electronic device comprising a first electrical contact, a second electrical contact, and a photoactive layer therebetween, wherein the photoactive layer comprises a luminescent compound having red, orange, or yellow emission color, a host material, and a compound having Formula I

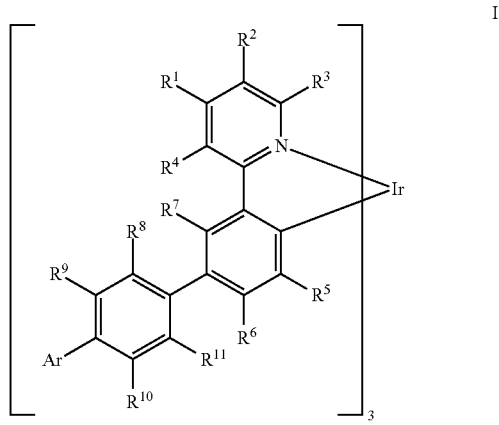

wherein:
Ar is selected from the group consisting of phenyl, biphenyl, and terphenyl, wherein Ar optionally has one or more substituents selected from the group consisting of D, alkyl, silyl, deuterated alkyl, and deuterated silyl;
$R^1$ is selected from the group consisting of H, D, alkyl, silyl, aryl, heteroaryl, deuterated alkyl, deuterated silyl, deuterated aryl, and deuterated heteroaryl; and
$R^2$-$R^{11}$ are the same or different and are selected from the group consisting of H, D, alkyl, silyl, deuterated alkyl, and deuterated silyl;
wherein the compound having Formula I is present as an electron-trap material which possesses a lowest unoccupied molecular orbital (LUMO) lying further in energy from the vacuum level than the LUMO of any other material present in the photoactive layer.

3. The device of claim 1, wherein the hole-trap material is present in an amount of 1-10 wt % based on the total weight of the photoactive layer.

4. The device of claim 1, wherein the hole-trap material is selected from compounds G1 through G6, G8, G11 through G13, and G15 through G17

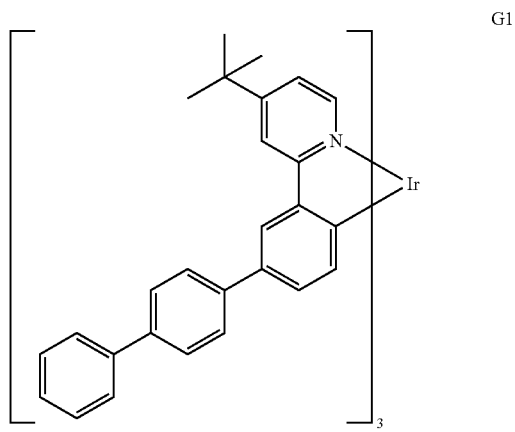

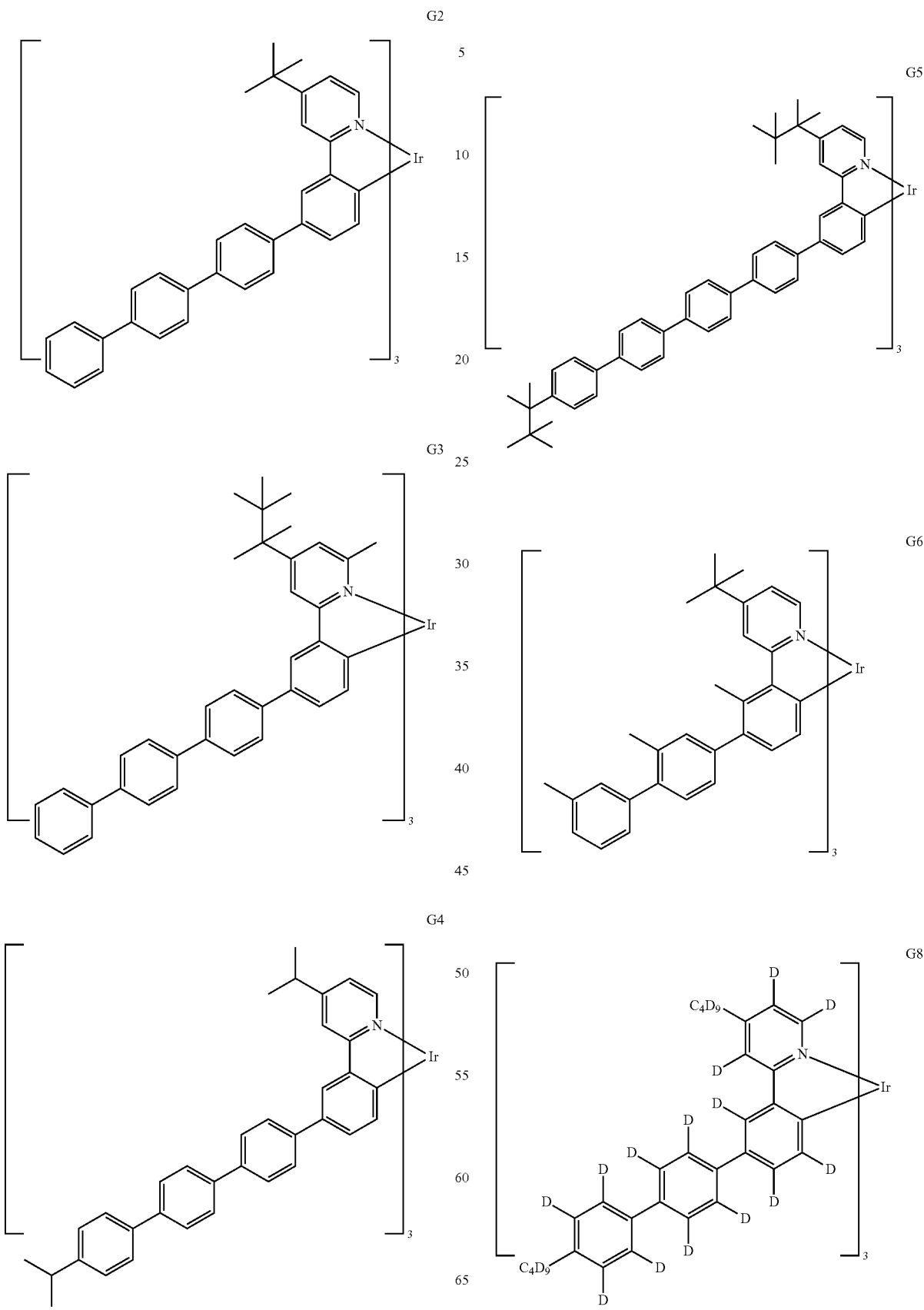

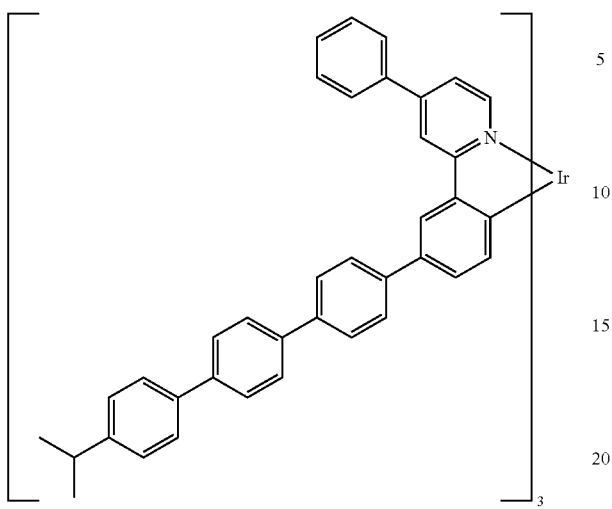
G11
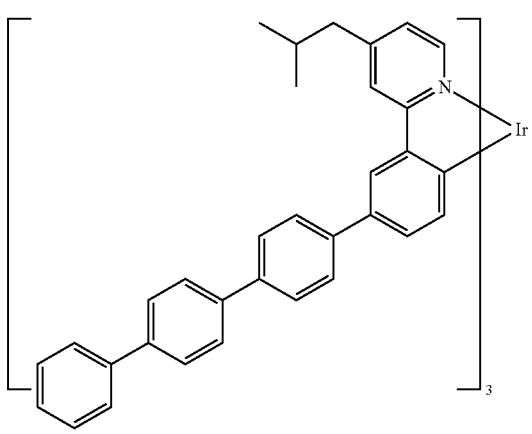
G15
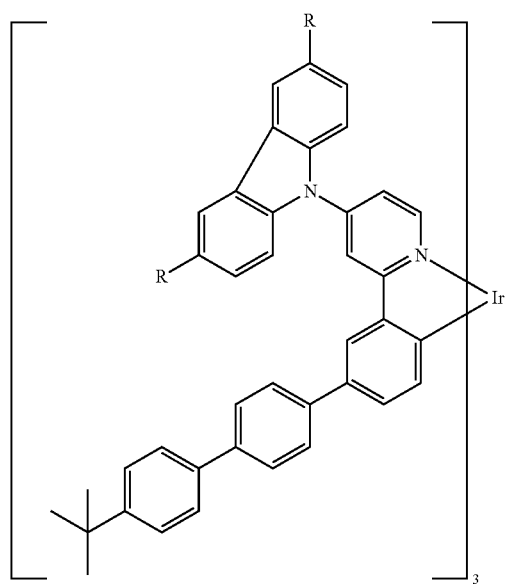
G12
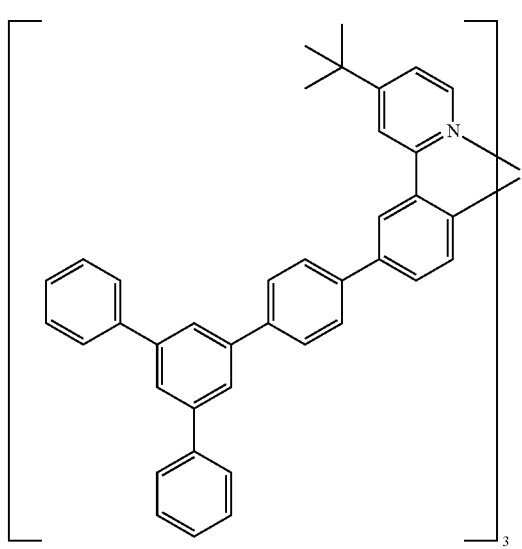
G13
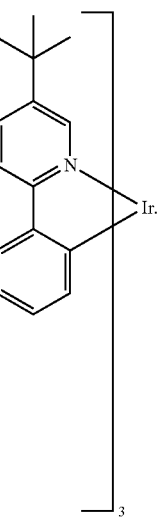
G16
G17
12a: R = phenyl
12b: R = 2-propyl
5. The device of claim 2, wherein the electron-trap material is present in an amount of 1-10 wt % based on the total weight of the photoactive layer.
6. The device of claim 2, wherein the electron-trap material is selected from compounds G1 through G6, G8, G11 through G13, and G15 through G17

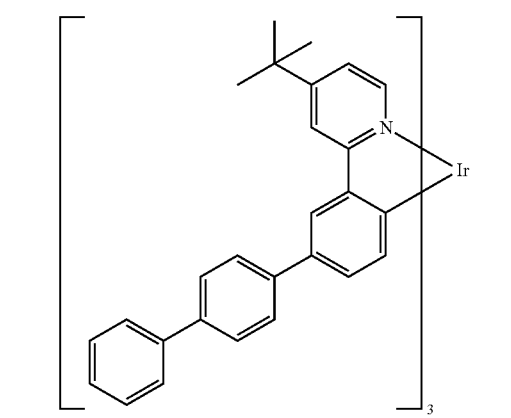
G1
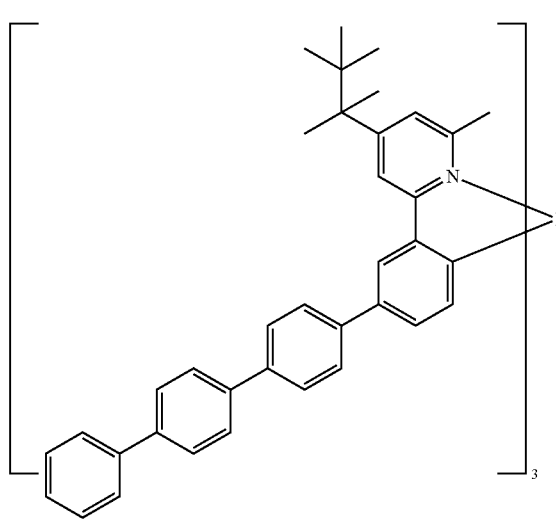
G2
G3
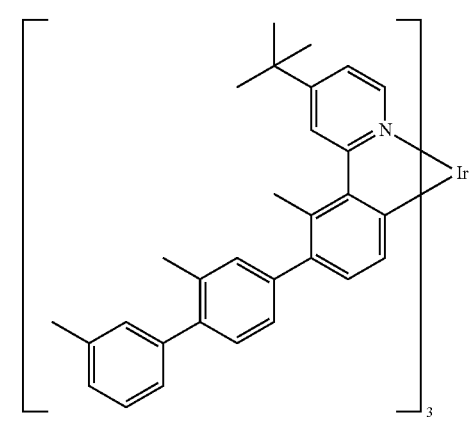
G4
G5
G6

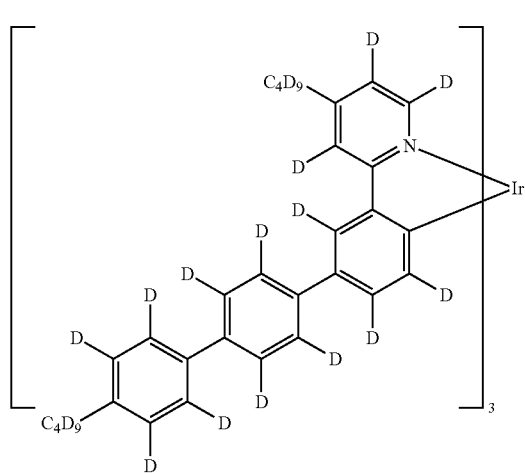
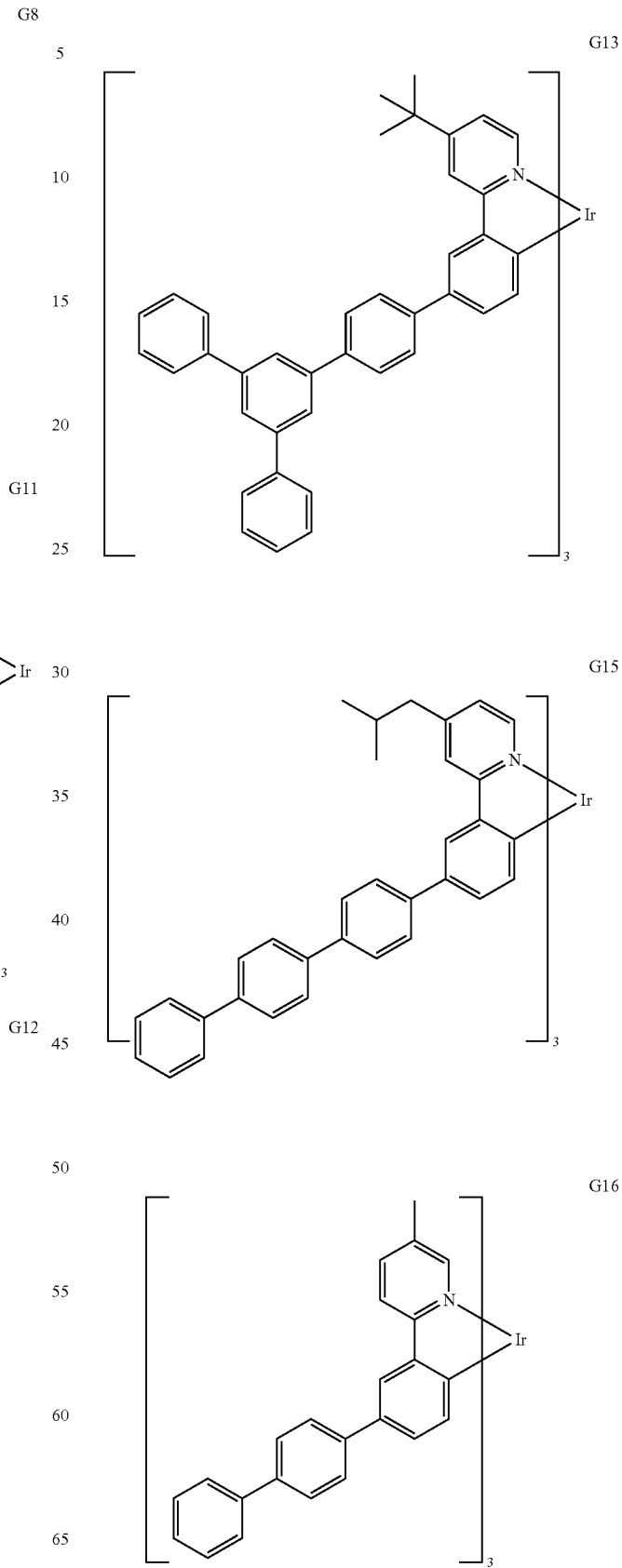

-continued

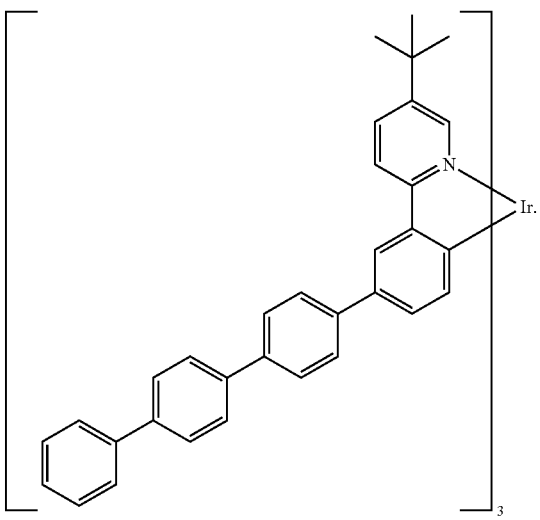

G17

12a: R = phenyl
12b: R = 2-propyl

7. The device of claim 1, wherein Ar is selected from the group consisting of phenyl, 3-biphenyl, 4-biphenyl, 4,4'-terphenyl, 4,3'-terphenyl, 3,4'-terphenyl, 3,3'-terphenyl, 3,5-terphenyl, substituted phenyl, substituted 3-biphenyl, substituted 4-biphenyl, substituted 4,4'-terphenyl, substituted 4,3'-terphenyl, substituted 3,4'-terphenyl, substituted 3,3'-terphenyl, substituted 3,5-terphenyl, and deuterated analogs thereof.

8. The device of claim 1, wherein $R^1$ is selected from the group consisting of alkyl having 1-20 carbons, silyl, deuterated alkyl having 1-20 carbons, and deuterated silyl.

9. The device of claim 1, wherein $R^1$ is selected from the group consisting of phenyl, naphthyl, biphenyl, terphenyl, substituted derivatives thereof, and deuterated analogs thereof.

10. The device of claim 1, wherein $R^1$ is selected from the group consisting of carbazolyl, phenyl-substituted carbazolyl, alkyl-substituted carbazolyl, and deuterated analogs thereof.

11. The device of claim 2, wherein Ar is selected from the group consisting of phenyl, 3-biphenyl, 4-biphenyl, 4,4'-terphenyl, 4,3'-terphenyl, 3,4'-terphenyl, 3,3'-terphenyl, 3,5-terphenyl, substituted phenyl, substituted 3-biphenyl, substituted 4-biphenyl, substituted 4,4'-terphenyl, substituted 4,3'-terphenyl, substituted 3,4'-terphenyl, substituted 3,3'-terphenyl, substituted 3,5-terphenyl, and deuterated analogs thereof.

12. The device of claim 2, wherein $R^1$ is selected from the group consisting of alkyl having 1-20 carbons, silyl, deuterated alkyl having 1-20 carbons, and deuterated silyl.

13. The device of claim 2, wherein $R^1$ is selected from the group consisting of phenyl, naphthyl, biphenyl, terphenyl, substituted derivatives thereof, and deuterated analogs thereof.

14. The device of claim 2, wherein $R^1$ is selected from the group consisting of carbazolyl, phenyl-substituted carbazolyl, alkyl-substituted carbazolyl, and deuterated analogs thereof.

* * * * *